(12) United States Patent
Auld

(10) Patent No.: US 9,888,975 B2
(45) Date of Patent: Feb. 13, 2018

(54) METHODS, SYSTEMS, AND DEVICES FOR CONTROL OF SURGICAL TOOLS IN A ROBOTIC SURGICAL SYSTEM

(71) Applicant: Ethicon Endo-Surgery, LLC, Guaynabo, PR (US)

(72) Inventor: Michael D. Auld, Cincinnati, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 123 days.

(21) Appl. No.: 14/959,262

(22) Filed: Dec. 4, 2015

(65) Prior Publication Data

US 2017/0156808 A1    Jun. 8, 2017

(51) Int. Cl.
*A61B 34/00*    (2016.01)
*A61B 90/50*    (2016.01)
(Continued)

(52) U.S. Cl.
CPC .............. *A61B 34/77* (2016.02); *A61B 34/30* (2016.02); *A61B 34/70* (2016.02); *A61B 90/50* (2016.02);
(Continued)

(58) Field of Classification Search
CPC ........ A61B 34/77; A61B 34/70; B25J 9/1689; B25J 9/023
(Continued)

(56) References Cited

U.S. PATENT DOCUMENTS 6,219,589 B1 * 4/2001 Faraz .................... B25J 9/1689
                                                         345/161
6,594,552 B1 * 7/2003 Nowlin .................. B25J 9/1689
                                                         318/568.11
(Continued)

FOREIGN PATENT DOCUMENTS

EP            2567669 A1    3/2013
WO    WO-2014151621 A1      9/2014
(Continued)

OTHER PUBLICATIONS

Mack, Minimally Invasive and Robotic Surgery, 2001, IEEE, p. 568-572.*
(Continued)

*Primary Examiner* — McDieunel Marc
(74) *Attorney, Agent, or Firm* — Mintz Levin Cohn Ferris Glovsky and Popeo, P.C.

(57) ABSTRACT

Techniques for a surgical system are provided that allow controlling a force applied by an electromechanical surgical tool coupled to an electromechanical surgical arm. A force limiter can be associated with at least one of the surgical arm and the tool and is used to limit the force applied by jaws of the tool to tissue when the tissue is engaged therebetween or when the tissue is otherwise manipulated. The force can be limited to a maximum force value, which can be preselected, and it can be adjustable based on user input or automatically. Also are provided techniques for a surgical system that allow controlling a stiffness of an electromechanical passive arm coupled to a fixture and having an active arm mounted
(Continued)

thereon. The stiffness is adjusted, either manually or automatically, by adjusting a friction at a joint of the arm based on an angle at the arm's joint.

21 Claims, 15 Drawing Sheets

(51) Int. Cl.
 *A61B 34/30* (2016.01)
 *A61B 90/00* (2016.01)
(52) U.S. Cl.
 CPC ... *A61B 2034/305* (2016.02); *A61B 2090/031* (2016.02); *A61B 2090/064* (2016.02); *A61B 2090/508* (2016.02)
(58) Field of Classification Search
 USPC .................................................. 700/245, 260
 See application file for complete search history.

(56) References Cited

U.S. PATENT DOCUMENTS

| | | | | |
|---|---|---|---|---|
| 6,859,683 | B2* | 2/2005 | Parker | B25J 19/023 318/567 |
| 6,879,880 | B2* | 4/2005 | Nowlin | B25J 9/1689 318/568.11 |
| 7,155,316 | B2* | 12/2006 | Sutherland | A61B 34/70 318/568.11 |
| 7,373,219 | B2* | 5/2008 | Nowlin | B25J 9/1689 318/568.11 |
| 7,778,733 | B2* | 8/2010 | Nowlin | B25J 9/1689 600/101 |
| 8,831,782 | B2 | 9/2014 | Itkowitz | |
| 2009/0202387 | A1 | 8/2009 | Dlugos, Jr. et al. | |
| 2011/0028894 | A1 | 2/2011 | Foley et al. | |
| 2012/0158013 | A1 | 6/2012 | Stefanchik et al. | |
| 2013/0103050 | A1 | 4/2013 | Richmond et al. | |
| 2013/0289767 | A1 | 10/2013 | Lim et al. | |
| 2015/0150635 | A1 | 6/2015 | Kilroy et al. | |
| 2017/0086932 | A1* | 3/2017 | Auld | A61B 34/71 |

FOREIGN PATENT DOCUMENTS

| | | |
|---|---|---|
| WO | WO-2014151952 A1 | 9/2014 |
| WO | WO-2015171614 A1 | 11/2015 |

OTHER PUBLICATIONS

International Search Report and Written Opinion for Application No. PCT/US2016/63904 dated May 16, 2017.

\* cited by examiner

METHODS, SYSTEMS, AND DEVICES FOR CONTROL OF SURGICAL TOOLS IN A ROBOTIC SURGICAL SYSTEM

FIELD

The present disclosure relates generally to methods, systems, and devices for control of surgical tools in a robotic surgical system.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Various robotic systems have been developed to assist in MIS procedures. Robotic systems can allow for more intuitive hand movements by maintaining both natural eye-hand axis. Robotic systems can also allow for more degrees of freedom in movement by including a "wrist" joint on the instrument, creating a more natural hand-like articulation. One drawback with robotic systems, however, is the loss of direct human contact with the tissue. It can be very difficult and expensive to give true force feedback to the surgeon. Another drawback is that robotic systems traditionally only allow the surgeon to control movement of up to two surgical instruments, with any other surgical instruments having to be manually controlled by other medical personnel. It can be difficult for the surgeon and other medical personnel to communicate and synchronize activities of the separately controlled instruments during performance of a surgical procedure.

Accordingly, there remains a need for improved methods, systems, and devices for control of surgical tools in a robotic surgical system.

SUMMARY

In one aspect, a surgical system is provided that in some embodiments includes an electromechanical arm configured for movement in multiple axes, an electromechanical tool mounted on the electromechanical arm, and a force limiter associated with at least one of the electromechanical arm and the electromechanical tool and configured to limit a force applied by at least one of the electromechanical arm and the electromechanical tool to cause movement of the electromechanical tool, the force being limited to a threshold force value.

The threshold force value can be selected in a number of ways and it can be any suitable value. For example, the threshold force value can be selected based on a user input. For another example, the threshold force value can be selected automatically. The threshold force value can be a maximum force value. The maximum force value can be adjustable via a user input system. As another example, the maximum force value can be adjustable via a force limiter associated with the electromechanical tool.

The force limiter can vary in a number of ways. For example, the force limiter can be or can include at least one mechanical component. The at least one mechanical component can be a slip clutch associated with the electromechanical tool. The force limiter can further include a force limiter adjustment mechanism. The at least one mechanical component can include a slip clutch coupled to first and second jaws of the electromechanical tool, and the force limiter adjustment mechanism can include at least one shim or at least one bellow disposed between the first and second jaws. In some embodiments, the force limiter can include at least one motor, and wherein current controlling torque of the at least one motor is used to control and limit the force applied by the electromechanical arm.

In other aspects, a method of operating a surgical system is provided that in some embodiments includes positioning an electromechanical arm of the surgical system in proximity to a patient's body, and manipulating an electromechanical tool mounted on the electromechanical arm to perform a surgical function, wherein a force applied by at least one of the electromechanical arm and the electromechanical tool to cause movement of the electromechanical tool is limited to a maximum force by a force limiter associated with at least one of the electromechanical arm and the electromechanical tool.

The method can vary in a number of ways. For example, the method can include receiving an input indicating a value of the maximum force. The input can vary in a number of ways a user input received via a user interface of a computing device.

In other aspects, a surgical system is provided that in some embodiments includes a passive arm having a first end configured to be coupled to a fixture and a second end, the passive arm having a joint between the first and second ends connecting first and second passive arm segments, the second end being configured to move toward and away from the fixture such that an angle between the first and second arm segments increases as a distance between the second end and the fixture increases, and an active arm coupled to the second end of the passive arm. The joint has a stiffness that is configured to proportionally decrease as the angle increases.

The surgical system can vary in a number of ways. For example, the stiffness of the joint can be automatically adjusted based on the angle. In at least some embodiments, the stiffness of the joint can be selectively controllable based on user input. In at least some embodiments, the stiffness of the joint can be automatically adjustable via a software-based controller.

The joint can also vary in a number of ways. For example, the joint can have an angle measurement sensor coupled thereto and configured to measure the angle. Additionally or alternatively, the joint can have a force sensor coupled thereto and configured to sense a force applied to the passive arm. In at least some embodiments, the joint can include a clutch mechanism.

In some embodiments, the system is configured to in response to detecting that a force is being applied to the joint to position the passive arm and thereby change the angle between the first and second arm segments, reduce a resistance of the joint to allow the passive arm to be repositioned to an other position; and after the passive arm is repositioned, and in response to detecting that the force is no longer being applied to the joint, increase the resistance of the joint to cause the joint to remain in the other position.

In further aspects, a method of operating a surgical system is provided that in some embodiments includes positioning an electromechanical surgical arm comprising a passive arm and an active arm coupled to the passive arm, the passive arm having first and second arm segments and a joint connecting the arm segments in proximity to a patient's body, wherein the first arm segment has a first end coupled to a fixture and a second end coupled to the active arm. The method further includes changing a position of the passive arm by moving the second arm segment such that an angle between the first and second arm segments increases as a distance between the second end and the fixture increases, and such that a stiffness of the joint proportionally decreases as the angle increases.

Non-transitory computer program products (i.e., physically embodied computer program products) are also provided that store instructions, which when executed by one or more processors of one or more computer systems, causes at least one processor to perform operations herein. Similarly, computer systems are also provided that can include one or more processors and one or more memories coupled to the one or more processors. Each of the one or more memories can temporarily or permanently store instructions that cause at least one processor to perform one or more of the operations described herein. In addition, methods can be implemented by one or more processors either within a single computer system or distributed among two or more computer systems. Such computer systems can be connected and can exchange data and/or commands or other instructions or the like via one or more connections, including but not limited to a connection over a network (e.g., the Internet, a wireless wide area network, a local area network, a wide area network, a wired network, etc.), via a direct connection between one or more of the multiple computer systems, etc.

BRIEF DESCRIPTION OF DRAWINGS

This disclosure will be more fully understood from the following detailed description taken in conjunction with the accompanying drawings, in which.

DETAILED DESCRIPTION

Figure 1:
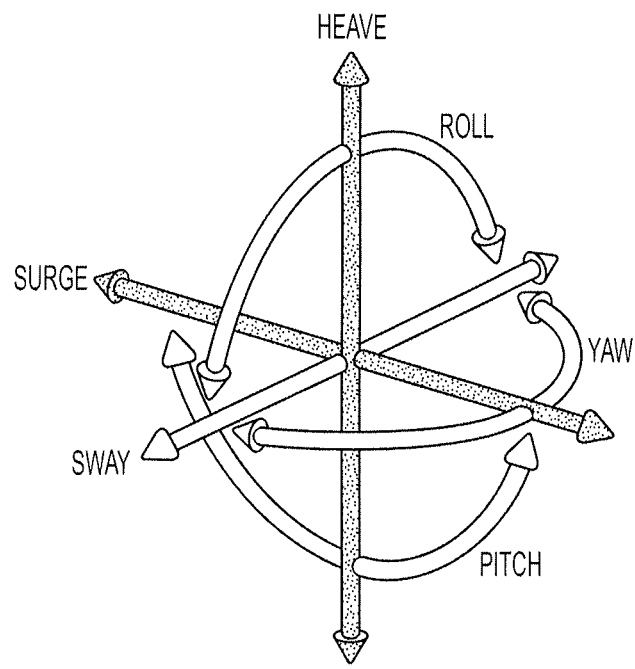
FIG. 1 is a graphical representation of terminology associated with six degrees of freedom.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present disclosure.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The present disclosure provides techniques for limiting a force applied by one or both of an electromechanical arm and an electromechanical tool coupled thereto of a robotic surgical system. The force is limited to avoid unintentional trauma to tissue as it is manipulated by the tool. Conventional surgical instruments having a tool, such as a tissue grasper, stapler, or other tissue-manipulating tool coupled thereto, allow only a manual control over a strength with which the tool engages the tissue. Thus, if a less experienced surgeon is using an instrument, the tissue can be pulled and/or squeezed too hard, which can cause its damage and can break a suture being used. Accordingly, force limiting techniques are provided that allow control over the force applied by the tool and/or arm. The force limiting techniques can be implemented using various force limiters, which can be or can include force limiting mechanisms and/or software-based force limiters.

The present disclosure also provides techniques for controlling stiffness of an electromechanical arm of a robotic surgical system. The electromechanical arm can be a passive arm mounted on an operating table or other platform and having an active arm coupled thereto. The passive arm needs to be positioned in a desired manner with respect to a patient laid on the operating table, to thereby properly position the active arm which has a surgical tool suitable for performing the surgical procedure coupled thereto. The passive arm's position may need to be changed during the surgery. However, the weight of the passive arm, as well as the weight of components mounted thereon, can complicate adjustment of the arm's position. Also, a precision of the positioning can be affected by the properties of the arm's joints. The described techniques provide a way to facilitate positioning of the arm, by controlling a friction of the arm's joint(s) to thereby control arm's stiffness. The arm's stiffness can be controlled such that, when a user moves the arm, the friction at the arm's joint changes accordingly, to thus facilitate user's manipulation of the arm.

Terminology

There are a number of ways in which to describe the movement of a surgical system, as well as its position and orientation in space. One particularly convenient convention is to characterize a system in terms of its degrees of freedom. The degrees of freedom of a system are the number of independent variables that uniquely identify its pose or configuration. The set of Cartesian degrees of freedom is usually represented by the three translational or position variables, e.g., surge, heave, sway, and by the three rotational or orientation variables, e.g., Euler angles or roll, pitch, yaw, that describe the position and orientation of a component of a surgical system with respect to a given reference Cartesian frame. As used herein, and as illustrated in FIG. 1, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right. In a more general sense, each of the translation terms refers to movement along one of the three axes in a Cartesian frame, and each of the rotational terms refers to rotation about one of the three axes in a Cartesian frame.

Although the number of degrees of freedom is at most six, a condition in which all the translational and orientational variables are independently controlled, the number of joint degrees of freedom is generally the result of design choices that involve considerations of the complexity of the mechanism and the task specifications. For non-redundant kinematic chains, the number of independently controlled joints is equal to the degree of mobility for an end effector. For redundant kinematic chains, the end effector will have an equal number of degrees of freedom in Cartesian space that will correspond to a combination of translational and rotational motions. Accordingly, the number of degrees of freedom can be more than, equal to, or less than six.

With regard to characterizing the position of various components of the surgical system and the mechanical frame, the terms "forward" and "rearward" may be used. In general, the term "forward" refers to an end of the surgical system that is closest to the distal end of the input tool, and when in use in a surgical procedure, to the end disposed within a patient's body. The term "rearward" refers to an end of the surgical system farthest from the distal end of the input tool, and when in use, generally to the end farther from the patient.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes includes various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

There are several general aspects that apply to the various descriptions below. For example, at least one surgical end effector is shown and described in various figures. An end effector is the part of a minimally invasive or invasive surgical instrument or assembly that performs a specific surgical function, e.g., forceps/graspers, needle drivers, scissors, electrocautery hooks, staplers, clip appliers/removers, suction tools, irrigation tools, etc. Any end effector can be utilized with the surgical system described herein. Further, in exemplary embodiments, an end effector can be configured to be manipulated by a user input tool. The input tool can be any tool that allows successful manipulation of the end effector, whether it be a tool similar in shape and style to the end effector, such as an input tool of scissors similar to end effector scissors, or a tool that is different in shape and style to the end effector, such as an input tool of a glove dissimilar to end effector graspers, and such as input tool of a joystick dissimilar to end effector graspers. In some embodiments, the input tool can be a larger scaled version of the end effector to facilitate ease of use. Such a larger scale input tool can have finger loops or grips of a size suitable for a user to hold. However, the end effector and the input tool can have any relative size.

A slave tool, e.g., a surgical instrument, of the surgical system can be positioned inside a patient's body cavity through an access point in a tissue surface for minimally invasive surgical procedures. Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any of the surgical system components disclosed herein can have a functional seal disposed thereon, therein, and/or therearound to prevent and/or reduce insufflation leakage while any portion of the surgical system is disposed through a surgical access port, such as a cannula. The surgical system can also be used in open surgical procedures. As used herein, a surgical access point is a point at which the slave tool enters a body cavity through a tissue surface, whether through a cannula in a minimally invasive procedure or through an incision in an open procedure.

Computer Systems

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 2:
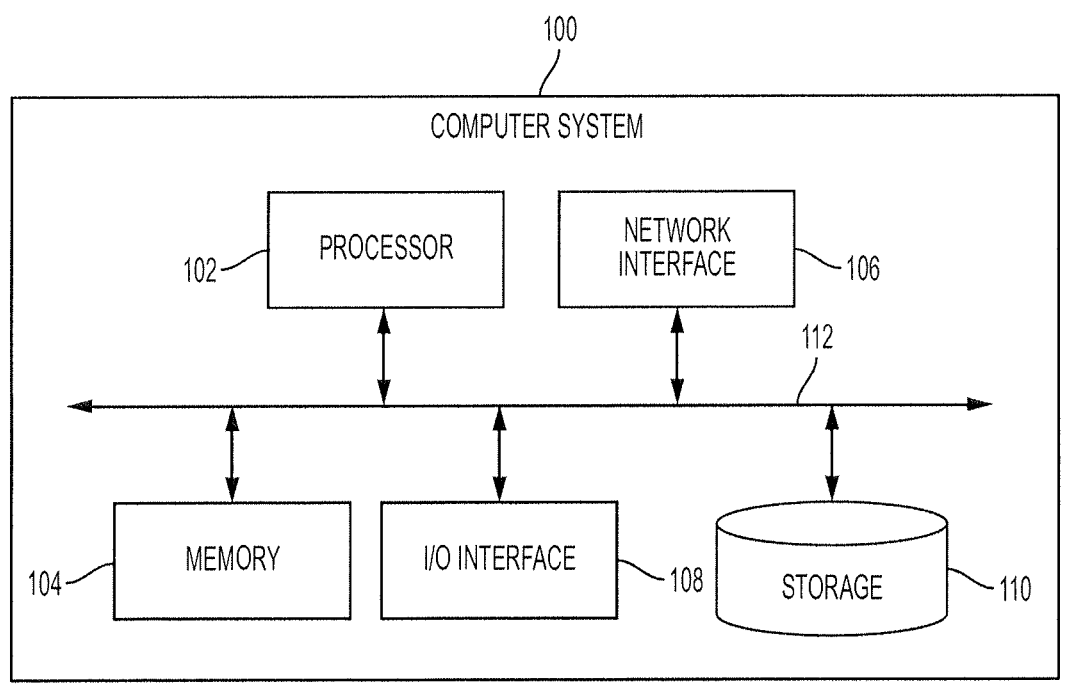
FIG. 2 is a schematic view of one embodiment of a computer system.

FIG. 2 illustrates one exemplary embodiment of a computer system 100. As shown, the computer system 100 can include one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (TO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN)

adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value is retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 2 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Robotic Surgical Systems

The systems, devices, and methods disclosed herein can be implemented using a robotic surgical system. Various embodiments of robotic surgical systems are described in further detail in U.S. Pat. No. 8,831,782 filed Jul. 15, 2013 entitled "Patient-Side Surgeon Interface For A Teleoperated Surgical Instrument," Intl. Pat. Pub. No. WO2014151621 filed Mar. 13, 2014 entitled "Hyperdexterous Surgical System," Intl. Pat. Pub. No. WO2014151952 filed Mar. 13, 2014 entitled "Compact Robotic Wrist," and U.S. Pat. Pub. No. 2012/0158013 filed Dec. 17, 2010 entitled "Surgical System And Methods For Mimicked Motion," which are hereby incorporated by reference in their entireties.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

Figure 3:
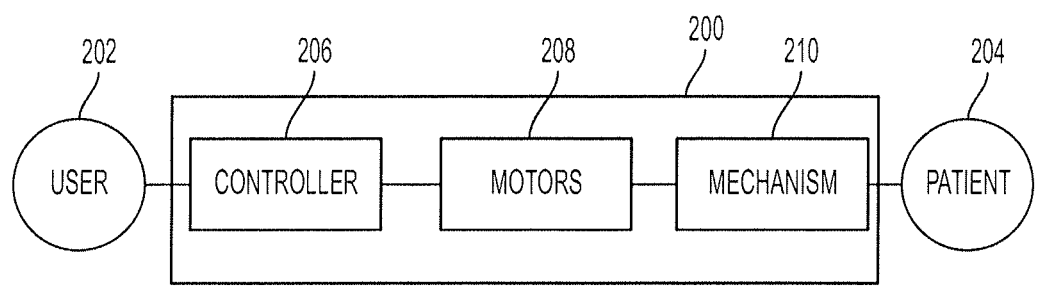
FIG. 3 is a schematic view of one embodiment of a robotic surgical system configured to be operated by a user and to be used during performance of a surgical procedure on a patient.

FIG. 3 illustrates an embodiment of a robotic surgical system 200 configured to be used by a user 202 (e.g., a surgeon, a surgical assistant, etc.) during performance of a surgical procedure on a patient 204. As in this illustrated embodiment, the robotic surgical system 200 can include a controller 206, motors 208, and a movement mechanism 210. The controller 206 can be configured to receive an input from the user 202 requesting movement, relative to the patient 204, of a surgical instrument coupled to the movement mechanism 210. The controller 206 can be configured to cause the motors 208 to drive movement of the movement mechanism 210, thereby causing the movement of the surgical instrument requested by the user 202. Although the illustrated robotic surgical system 200 includes a plurality of motors 208, a robotic surgical system can include a single motor. Similarly, although the illustrated robotic surgical system 200 includes a single controller 206 and a single movement mechanism 210, a robotic surgical system can include a plurality of controllers and/or a plurality of movement mechanisms.

In an exemplary embodiment, the movement mechanism 210 can include an arm. The arm can be configured to move so as to cause movement of a surgical instrument coupled thereto in any one or more of the three translational directions (surge, heave, and sway) and in any one or more of the three rotational directions (roll, pitch, and yaw) in response to control by the controller 206. In an exemplary embodiment, the arm can be configured to provide a plurality of degrees of freedom. More than six degrees of freedom can be provided in a variety of ways, as mentioned above and as will be appreciated by a person skilled in the art. In general, the arm can include a mechanical member configured to move in response to an input to the system 200 from the user 202. The user's input can be configured to cause the controller 206 to transmit an electronic signal to the motors 208 that causes the motors 208 to provide a force (e.g., torque) to the arm, thereby causing movement of the arm. The arm can include a plurality of members jointed together, which can facilitate movement of the arm in a plurality of degrees of freedom via bending, twisting, etc. at various ones of the joints.

The arm can include an electromechanical arm. The electromechanical arm can include one or more mechanical members configured to move in response to an electronic input. Examples of mechanical members that can form the arm include elongate shafts, coupling mechanisms (e.g., clips, magnets, snap fit mechanisms, shaped members configured to seat an instrument therein by interference fir or press fit, clamps, protrusions configured to be seated in corresponding depressions formed in a surgical instrument, depressions configured to receive therein corresponding protrusions extending from a surgical instrument, etc.) configured to removably and replaceably couple a surgical instrument to the arm, and joints (e.g., hinges, gimbals, etc.).

Figure 4:
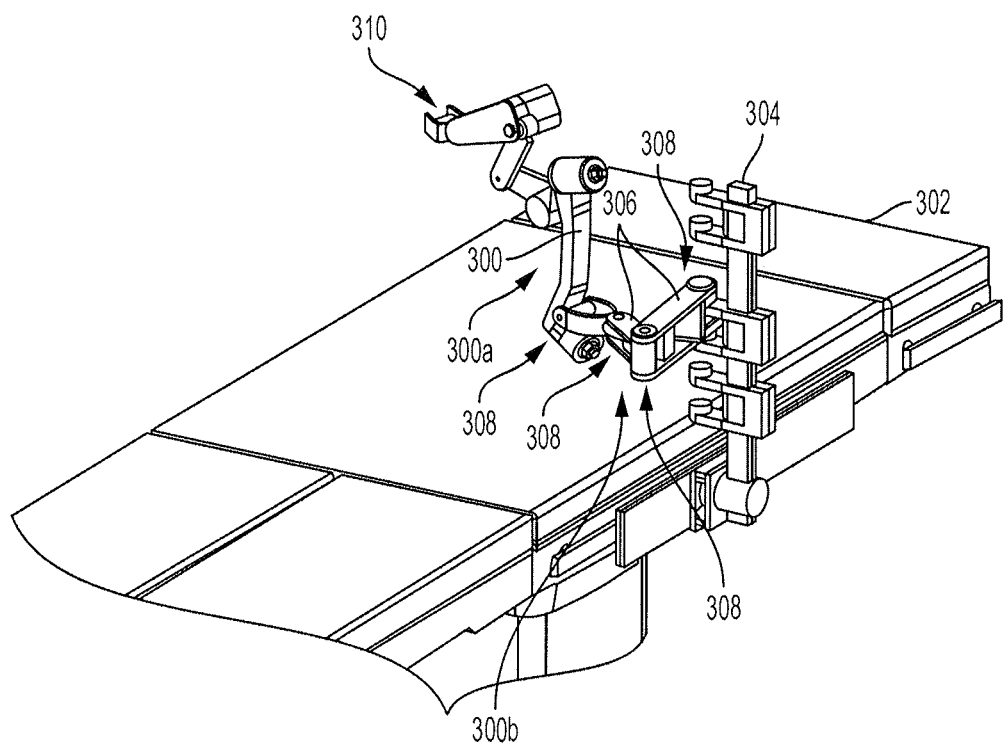
FIG. 4 is a perspective view of one embodiment of an arm of a robotic surgical system, the arm being mounted to a surgical table.
Figure 5:
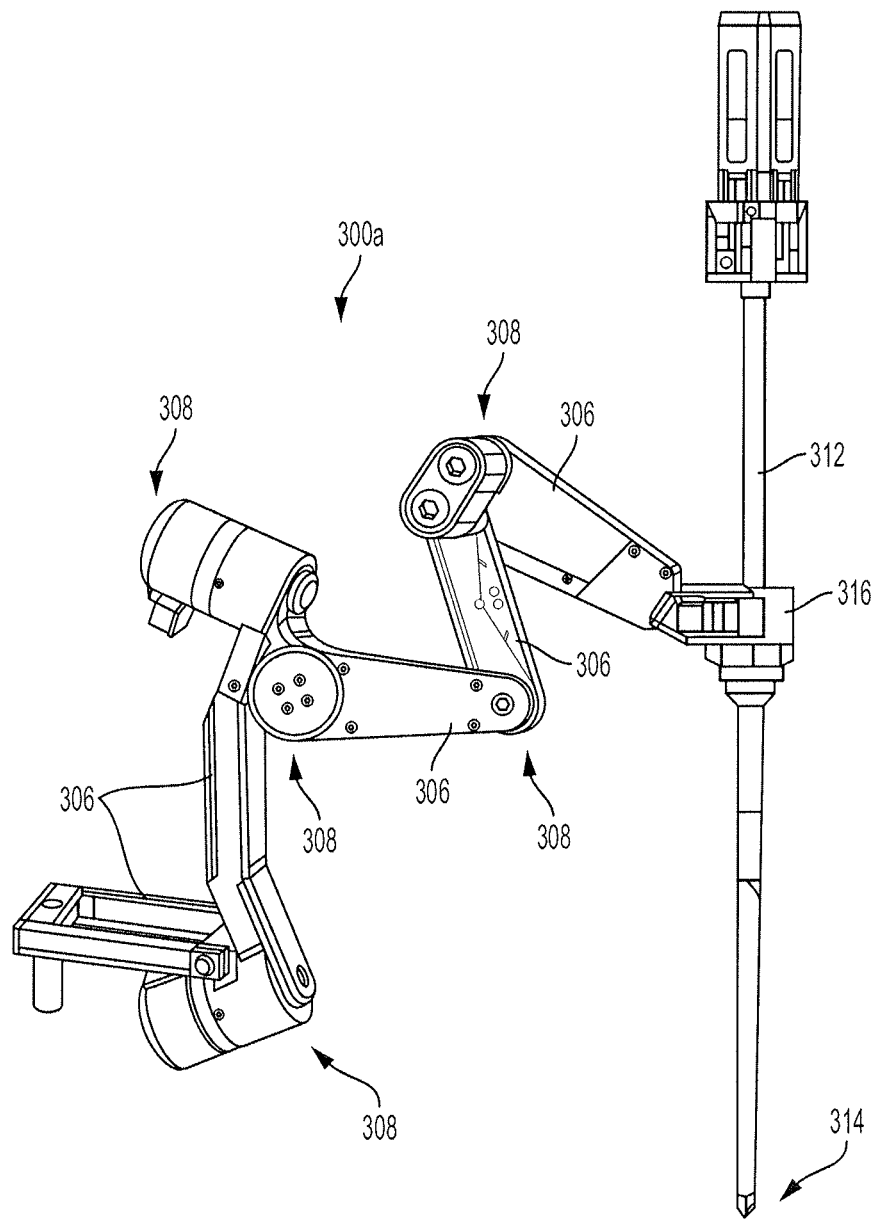
FIG. 5 is a perspective view of an active portion of the arm of FIG. 4.

FIGS. 4 and 5 illustrate an embodiment of an arm 300 in the form of an electromechanical arm. The arm 300 is mounted to a surgical table 302 using a frame 304 in the illustrated embodiment of FIG. 4, but the arm 300 can be mounted to any of a variety of stationary items, a wall, a table, a cart, the ceiling, etc., in any of variety of ways to help stabilize the arm 300 for use during a surgical procedure. The arm 300 can include an active portion 300a configured to be actively controlled, e.g., configured to move in response to electronic input, and a passive portion 300b configured to be passively controlled, e.g., configured to move in response to hand or other manual movement thereof. The passive portion 300b can lack motors or other electrical features, while the active portion 300a can include motors and other electrical features, such as associated with the joints, to facilitate electronic control thereof. In at least some embodiments, an arm can lack a passive portion so as to be configured to be entirely actively controlled. While the active and passive portions 300a, 300b are sometimes referred to herein as components of a single arm, a person skilled in the art will appreciate that the active portion 300a and the passive portion 300b can be separate arms that are matable to each other.

The arm 300 can, as in this illustrated embodiment, include a plurality of mechanical members 306, a plurality of joints 308, and a coupling mechanism 310. Adjacent ones of the mechanical members 306 can be attached together at one of joints 308. In this illustrated embodiment, the active portion 300a of the arm 300 includes five mechanical members 306 and four joints 308, the passive portion 300b of the arm 300 includes two mechanical members 306 and three joints 308, and the arm 300 includes another joint 308 between the active and passive portions 300a, 300b, but arms can have any number of mechanical members and associated joints in its active and passive portions.

As shown in FIG. 5, the arm 300, e.g., the active portion 300a thereof, can be configured to removably and replaceably couple to a surgical instrument 312 via the coupling mechanism 310. A distal end 314 of the instrument 312 can be configured to be advanced into a body of a patient, e.g., through an incision, through a natural orifice, etc. The instrument's distal end 314 can thus include a working end of the instrument 312 configured to facilitate performance of the surgical procedure within the patient. The instrument's distal end 314 can include an end effector, e.g., forceps/graspers, needle drivers, scissors, electrocautery hooks, staplers, clip appliers/removers, suction tools, irrigation tools, etc. As in this illustrated embodiment, the instrument 312 can be advanced into a patient's body through a cannula 316 (e.g., a trocar, an introducer tube, etc.). The coupling mechanism 310 is shown in FIG. 5 coupled to the cannula 316, which has the surgical instrument 312 advanced therethrough.

Aspects of the arm 300 and the frame 304 are further described in previously mentioned Intl. Pat. Pub. No. WO2014151621 filed Mar. 13, 2014 entitled "Hyperdexterous Surgical System" and Intl. Pat. Pub. No. WO2014151952 filed Mar. 13, 2014 entitled "Compact Robotic Wrist."

Figure 6:
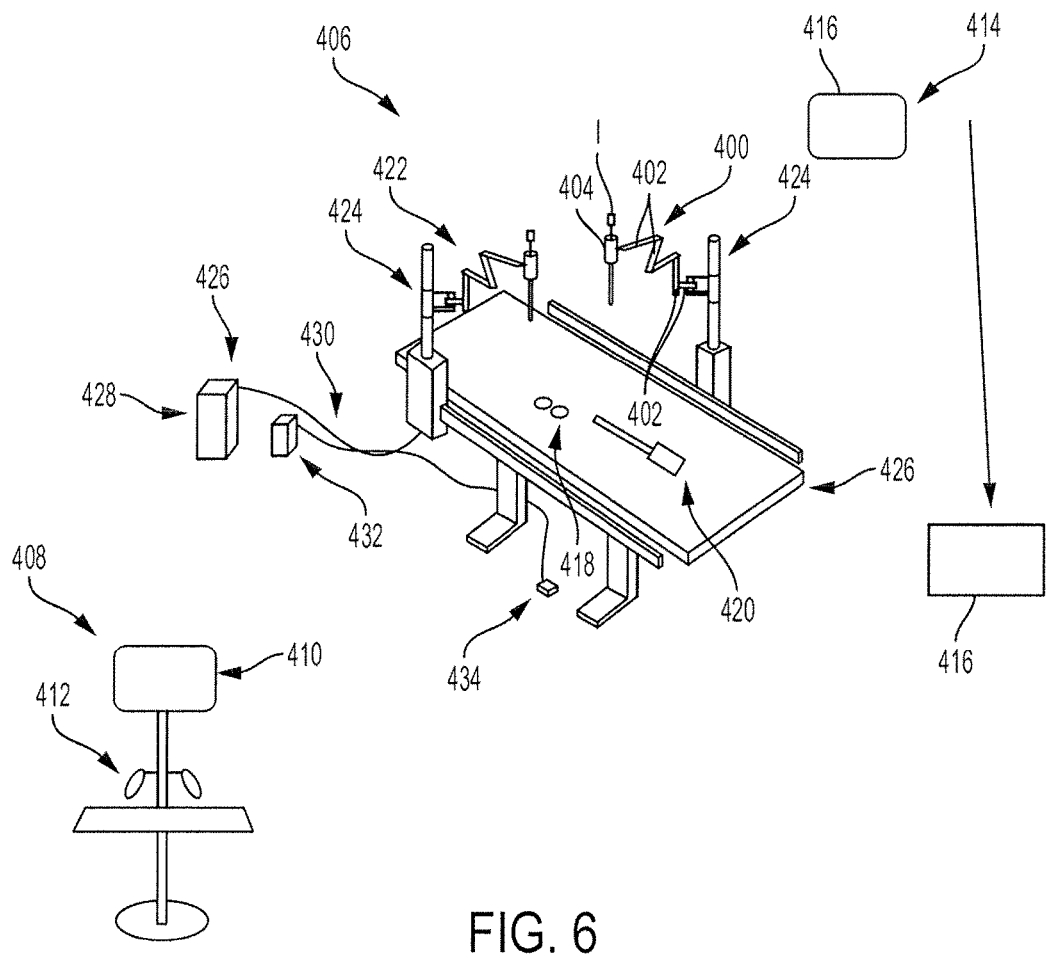
FIG. 6 is a perspective view of one embodiment of a robotic surgical system.

FIG. 6 illustrates another embodiment of an arm 400 in the form of an electromechanical arm. The arm 400 can generally be configured and used similar to the arm 300 of FIGS. 4 and 5. The arm 400 can include a plurality of mechanical members 402, a plurality of joints between adjacent ones of the mechanical members 402, and a coupling mechanism 404 configured to removably and replaceably couple to a surgical instrument I. The arm 400 includes five mechanical members 402 and four joints in this illustrated embodiment, but as mentioned above, arms can have any number of mechanical members and associated joints.

Figure 7:
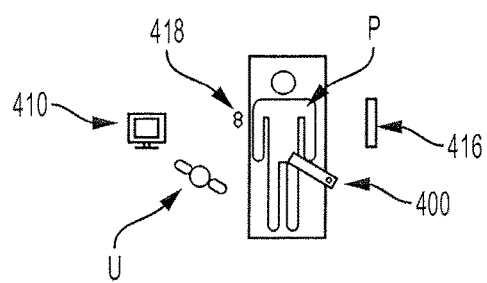
FIG. 7 is a schematic view of one embodiment of the robotic surgical system of FIG. 6 in use during performance of a surgical procedure on a patient.
Figure 8:
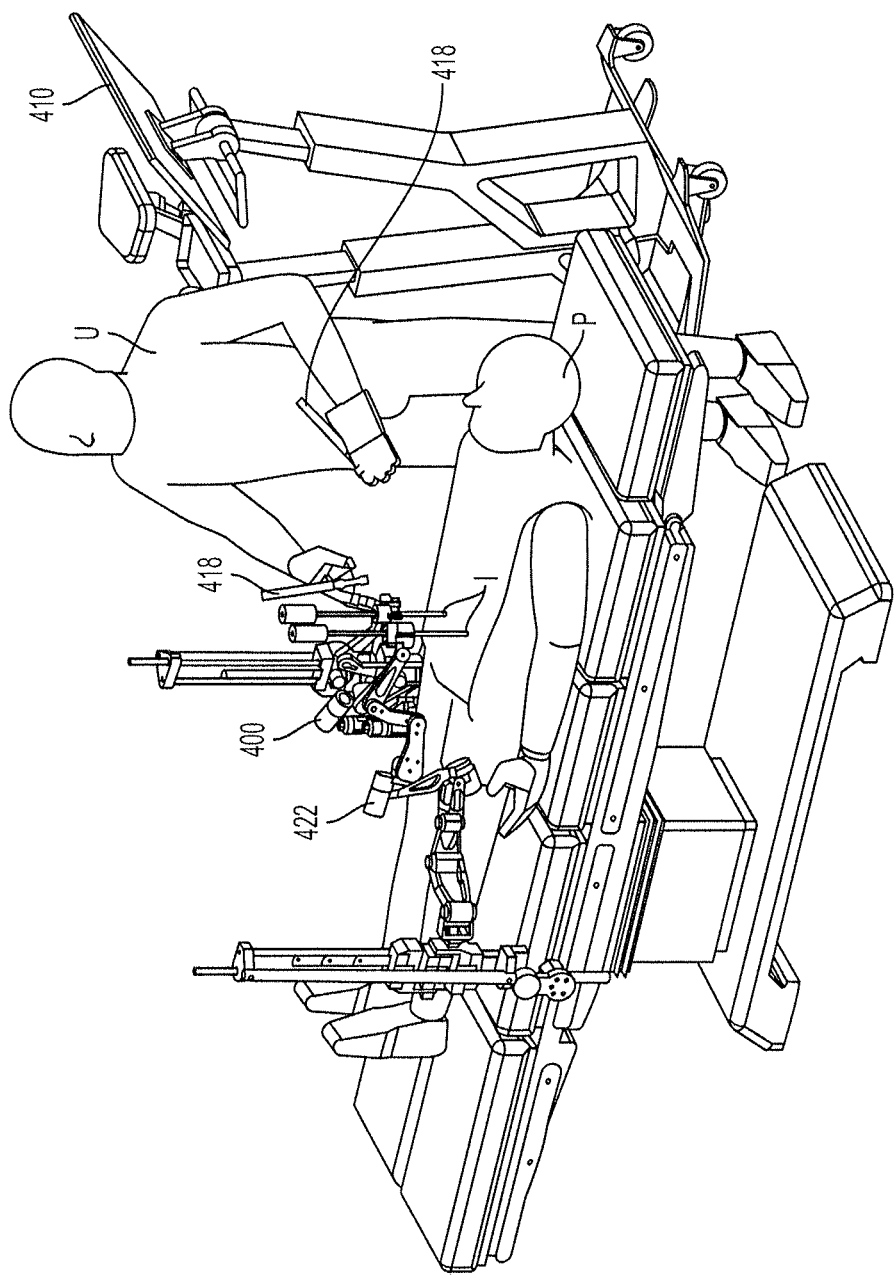
FIG. 8 is a perspective view of the robotic surgical system of FIG. 7 in use during performance of the surgical procedure on a patient.

As shown in FIGS. 6 and 7, the arm 400 can be included in a robotic surgical system 406 configured to facilitate performance of a surgical procedure on a patient P. FIG. 8 shows an example of the system 406 in use. As in this illustrated embodiment, the system 406 can include a user interface sub-system 408 that can include at least one display 410 configured to display information thereon to a user U, at least one user input device 412 configured to receive a user input thereto to control movement of the arm 400, a visualization system 414 that can include at least one display 416 configured to display thereon image(s) of a surgical procedure being performed using the system 406, a freely movable user input device 418 (shown as pinchers in this illustrated embodiment) configured to receive a user input thereto to control movement of the arm 400 and configured to be freely moved around by the user U (e.g., handheld and moved around any space in or near an operating room, etc.), an additional arms 422 that can be configured and used similar to the arm 400, and a control system 426 configured to facilitate control of the arms 400, 422 by translating user inputs to the user input devices 412, 418, e.g., manual movement of a user input device, movement indicated by touch on a touch screen, etc., to one or both of the arms 400, 422 as appropriate. The system 406 in this illustrated embodiment includes two arms 400, 422, but it can include another number of arms, e.g., three, four, etc. The at least one display 410 of the user interface sub-system 408 can be configured as a user input device, e.g., as a touchscreen configured to receive user touch input thereon. The user interface sub-system 408 can be in the same room as the patient P, or it can be in a different room.

The control system 426 can, as in this illustrated embodiment, include at least one computer 428, one or more cables 430, and at least one power supply 432. The computer 428 can include at least one processor (not shown). As mentioned above, some embodiments of control systems can be at least partially wireless, in which case at least some of the cables 430 need not be present. The robotic surgical system 406 can include at least one foot pedal 434 coupled to the computer 428 via one of the cables 430, which can allow the foot pedal 434 to serve as a user input device.

The robotic surgical system 406 can include a frame 424 for each of the arms 400, 422. The frames 424 in this illustrated embodiment are each mounted to a surgical table 426, but as mentioned above, frames can be mounted elsewhere. The frame 424 in this illustrated embodiment includes a vertical extension movably coupled to a rail mounted to the table 426. The vertical extension can be configured to move along the rail, thereby facilitating positioning of the arms 400, 422 relative to the patient P.

One or more manually operated surgical instruments 420, e.g., instruments not under the control of the robotic surgical system 406, can be used to perform the surgical procedure being performed on the patient P.

Aspects of the robotic surgical system 406 are further described in previously mentioned Intl. Pat. Pub. No. WO2014151621 filed Mar. 13, 2014 entitled "Hyperdexterous Surgical System."

Figure 9:
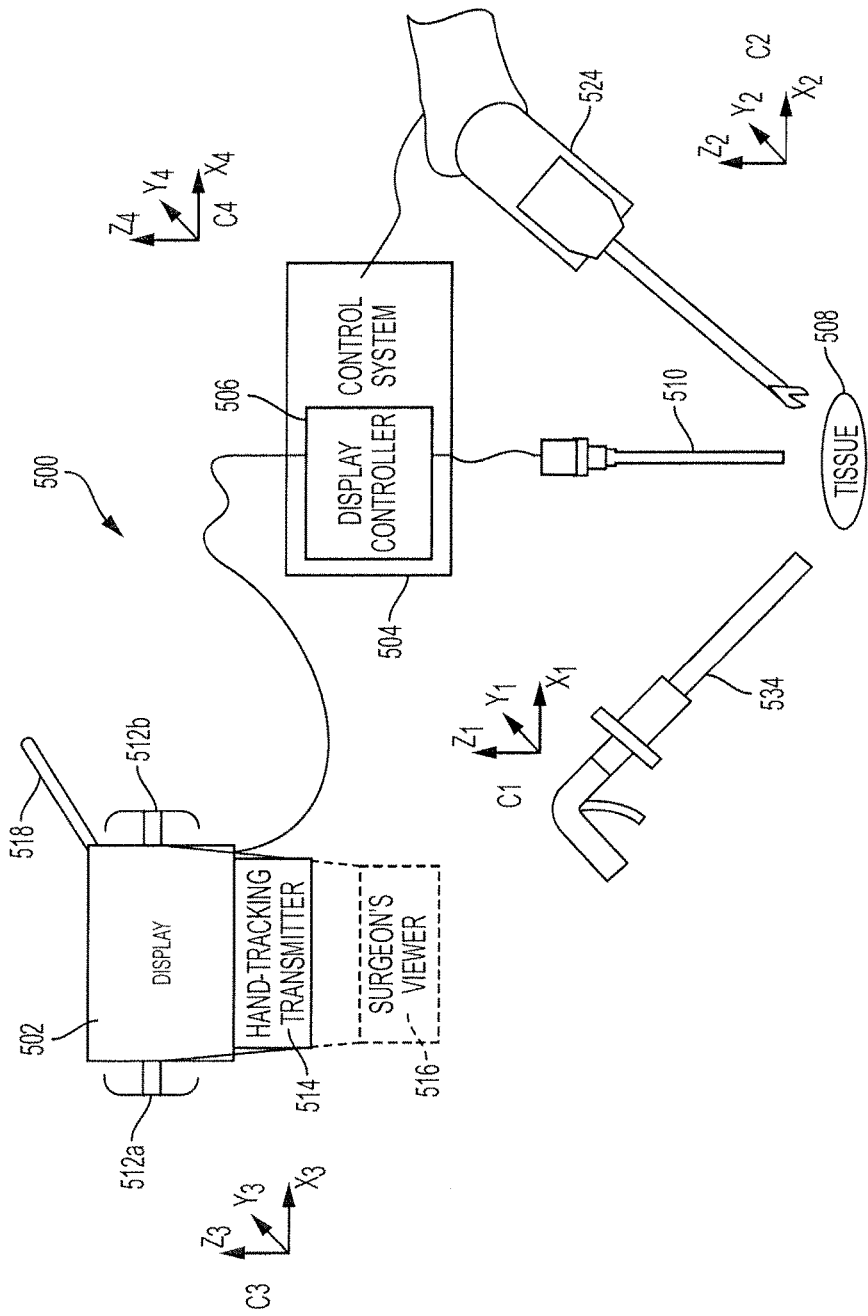
FIG. 9 is a schematic and perspective view of another embodiment of a robotic surgical system.

FIG. 9 illustrates another embodiment of a robotic surgical system 500. As in this illustrated embodiment, the robotic surgical system 500 can include a display 502 and a control system 504 configured to be in electronic communication with the display 502. The display 502 and the control system 504 are in wired electronic communication in this illustrated embodiment, but the electronic communication can be wireless. The control system 504 can include a computer system including a display controller 506 configured to facilitate the display of images on the display 502, such as images of tissue 508 visualized by an endoscope 510 coupled to the control system 504. The display 502 can be coupled to handles 512a, 512b configured to facilitate manual movement of the display 502, a hand-tracking transmitter 514 configured to generate a field (e.g., an electromagnetic field, an optical field (e.g., light beams), etc.), a surgeon's viewer 516 (e.g., glasses, etc.) configured to facilitate three-dimensional (3-D) viewing of 3-D images shown on the display 502, and a boom 518 configured to mount the display 502 to a stable surface (e.g., a wall, a table, etc.). The display 502 can be configured to show two-dimensional (2-D) and/or 3-D images.

Figure 10:
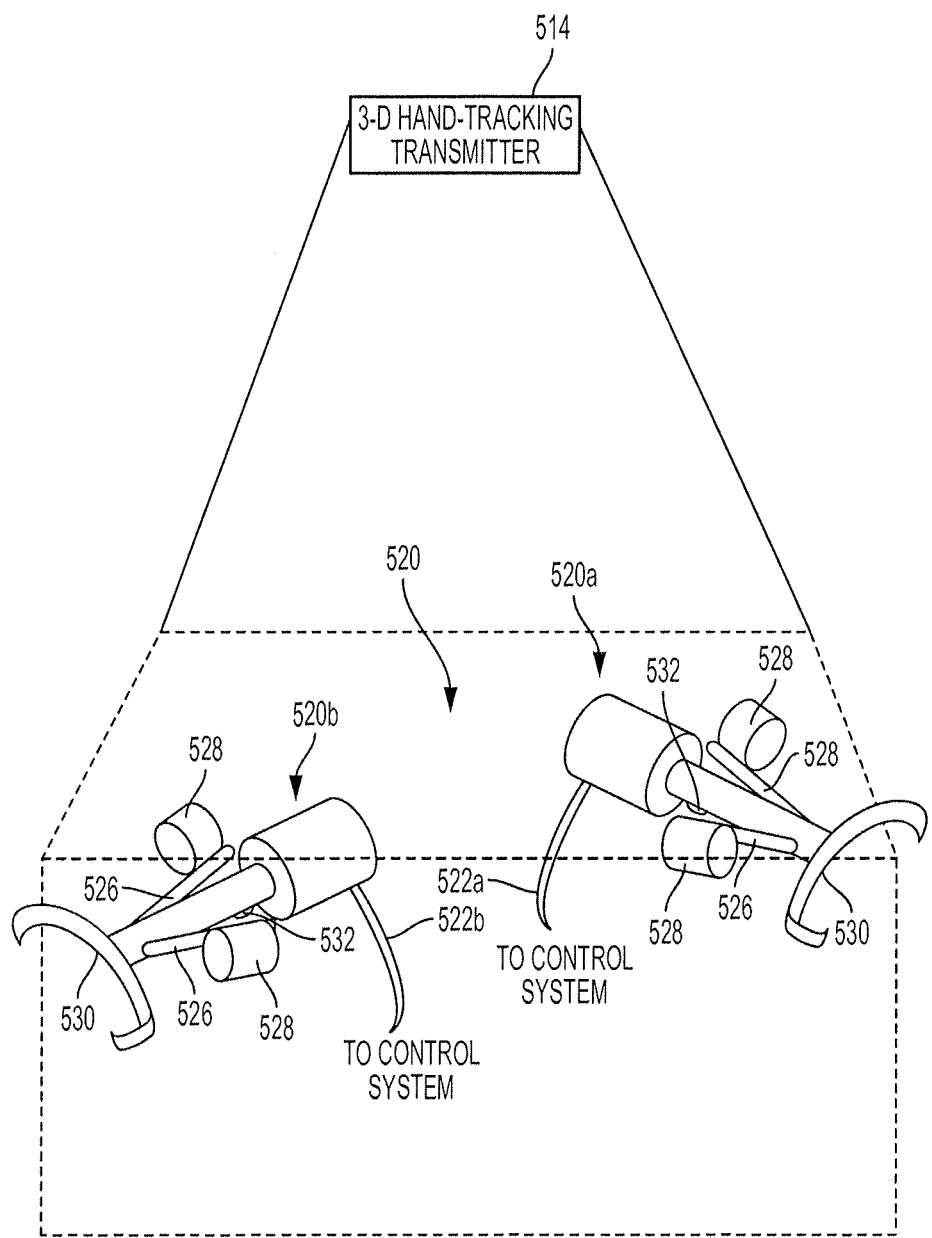
FIG. 10 is a perspective view of one embodiment of a master tool in a field generated by a transmitter of the robotic surgical system of FIG. 9.

Movement of a user-controlled master tool 520, an embodiment of which is illustrated in FIG. 10, in the field generated by the transmitter 514 can be configured to provide sensed spatial position and orientation information in a 3-D coordinate system. The master tool 520 can be configured to transmit the spatial position and orientation information to the control system 504, such as by cables 522a, 522b. The control system 504, e.g., a processor thereof, can be configured to receive the transmitted spatial position and orientation information and, in response thereto, cause a slave tool 524 to move in accordance with the user's movement of the master tool 520. The robotic surgical system 500 can thus allow control of the slave tool 524 via the master tool 520. The master tool 520 in this illustrated embodiment includes first and second master tool grips 520a, 520b that each include a plurality of levers 526, a plurality of finger loops 528, a palm rest 530, and a mode control button 532, but the master tool 520 can have a variety of other configurations, as will be appreciated by a person skilled in the art. The robotic surgical system 500 can include any number of master tools and any number of slave tools each configured to be controlled by the master tool(s).

One or more manually operated surgical instruments 534 can be used to manipulate the tissue 508 in addition to the slave tool 524 that can manipulate the tissue 508.

FIG. 9 illustrates first, second, third, and fourth coordinate systems C1, C2, C3, C4 representing local coordinates that specify the respective position and orientation of the portion of the system 500 with which they are associated. The first coordinate system C1 is associated with the manually operated surgical instrument 534. The second coordinate system C2 is associated with the slave tool 524. The third coordinate system C3 is associated with a user (not shown) visualizing the display 502, and hence also with the master tool 520 configured to be manipulated by the user. The fourth coordinate system C4 is associated with the control system 506, and hence also with images that the control system 506 causes to be displayed on the display 502. In general, the control system 506 can be configured to map and translate the third coordinate system C3 into the second coordinate system C2, e.g., map and translate movement of the master tool 520 to movement of the slave tool 524. The control system 506 can be configured to always orient the display 502 so that the first, second, and third coordinate systems C1, C2, C3 are aligned to the third coordinate system C3. For example, if the user is holding the master tool 520, e.g., one of the first and second master tool grips 520a, 520b, in one of his/her hands and moves that hand to his/her right, thereby moving the held master tool 520 to the right, the control system 506 can be configured to correspondingly cause a working end of the slave tool 524 to move to the right. This movement can be accomplished by the control system 506 causing an arm to which the slave tool 524 is coupled, similar to the arms discussed herein, to move. This movement of the slave tool 523 can "correct" for pivoting of a trocar (not shown) through which the slave tool 524 may be inserted to access the tissue 508.

Aspects of the robotic surgical system 500 are further described in previously mentioned U.S. Pat. No. 8,831,782 filed Jul. 15, 2013 entitled "Patient-Side Surgeon Interface For A Teleoperated Surgical Instrument."

Some robotic surgical systems have tools or end effectors (e.g., jaws, tissue graspers, etc.) that are capable of applying forces of a high magnitude (e.g., compressive and tensile forces) to affected tissue or to an instrument or device affecting tissue. Because the robotic surgical systems are typically configured such that no feedback is generated for a surgeon to assess the amount of force applied to tissue, surgeons typically manually control the force applied to tissue based on their experience. Thus, when a less experienced person performs a surgery, or when a surgeon misjudges the applied force, unintended tissue trauma can be caused as a result of excessive force being applied to the tissue. Another undesired consequence of the lack of control over the applied forces is the potential for suture to be damaged or broken when a tool and/or an arm is used to pull the tissue with an excessive force. The lack of control over the applied forces can thus compromise the efficiency and/or outcome of the surgery.

Accordingly, some embodiments provide a force limiting technique to control and limit a force applied to tissue by a surgical tool or end effector. The applied force can be controlled such that it cannot exceed a predetermined threshold force. Such a threshold force can be the maximum force value that a surgical tool (e.g., jaws or other tissue grasping tips) can apply to tissue before deflecting or otherwise becoming unable to apply a greater force. Once the maximum force value is established, the surgical tool can be used with little or no risk of damaging tissue as a result of the application of excessive force. As explained below, such force limiting techniques can be implemented in one or more mechanical components. Additionally or alternatively, the techniques can be implemented as one or more software components, or as a combination of hardware and software.

A force limiter can be associated with at least one of an electromechanical arm and an electromechanical surgical tool or end effector mounted to the arm. The force limiter can be configured such that, during movement or use of at least one of the electromechanical arm and the electromechanical surgical tool, the force applied as a result of such movement or use is limited to a threshold force value. When the force is limited in a mechanical way, a maximum force value can be set up based on a user input received by a force limiting adjustment component. When software component(s) are used to control the force, user input can be received via a suitable input device, such as a user interface of system 408 shown in FIG. 6 above, or via another device. Regardless of the way in which the maximum force value is established, it can have various values. For example, novice users can set a lower value, whereas more experienced users can use larger maximum force values. The force limiter can be implemented such as a user can establish a maximum force value based on various factors, such as a type of procedure, a type of tissue, a type of suture, previously used maximum force values (which can be logged in a suitable storage device), and other relevant factors.

A force limiting mechanism can be disposed at a number of different locations on a surgical instrument. For example, it can be disposed on one or more electromechanical arms and/or on one or more electromechanical surgical tools.

Figure 11:
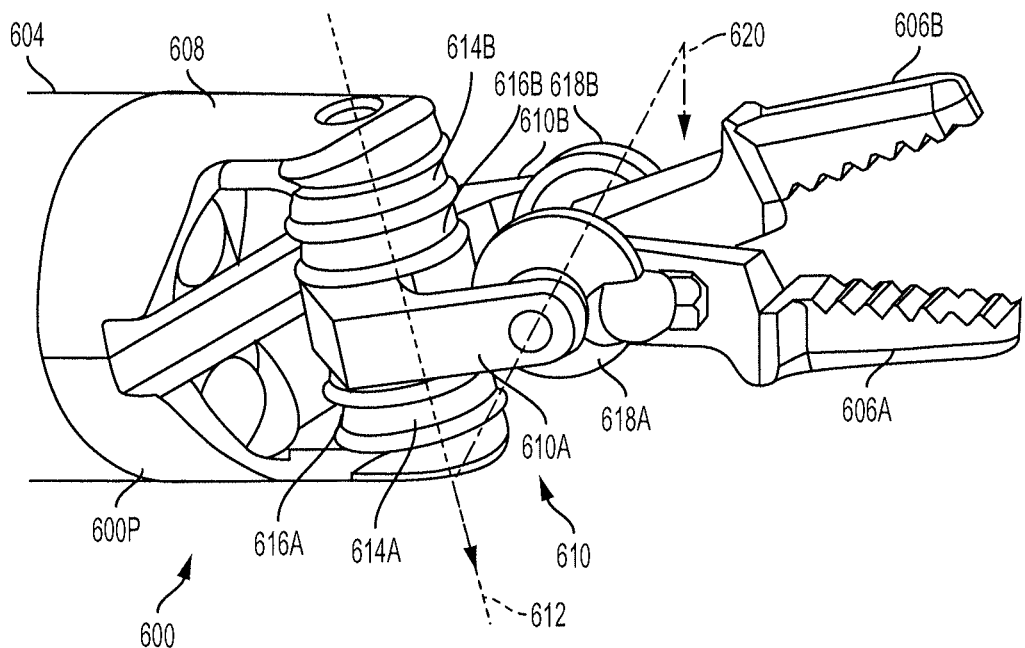
FIG. 11 is a perspective view of one embodiment of an electromechanical tool of a surgical instrument.

The force limiter can have a number of different configurations. In some embodiments, it can be implemented as a slip clutch. FIG. 11 illustrates an example of an end effector end or an electromechanical surgical tool 600 configured to perform a surgical function and which can include a force limiter in accordance with the described techniques. The tool 600 can be mounted on a distal end of a shaft 604 of a surgical instrument of a surgical system, such as a robotic surgical system (not shown). The surgical instrument can be removably and replaceably coupled to an electromechanical arm, such as an active arm or a passive arm of a robotic surgical system. The electromechanical arm can be configured for movement in multiple axes. As discussed above, the electromechanical arm can be coupled to a fixture which can be any suitable support member or other component.

In this example, the tool 600 can be an end effector in the form of a grasper mechanism including a pair of jaws 606A, 606B. The tool 600 can be implemented, for example, similar to a tool of a robotic surgical system described in U.S. Pat. Pub. No. 2015/0150635 filed Sep. 25, 2014, entitled "Compact Robotic Wrist," which is hereby incorporated by reference in its entirety. It should be appreciated, however, that the tool can be or can include other types of end effectors, as the described techniques are not limited to any specific type(s) of an end effector.

As shown in FIG. 11, a proximal end 600p of the tool 600 can have a yoke 608 coupled to the shaft 604. The yoke 608 is movably coupled to a second yoke 610 having brackets 610A, 610B via an extended axle (not shown) that extends along an axis 612. The axle can be removable or integrally formed with the second yoke 610 or the yoke 608. Additionally or alternatively, any other element can be used to movably couple the yokes 608, 610 to one another. The tool 600 further includes drive pulleys 614A, 614B, 616A, 616B coupled to the extended axle and arranged along the axis 612 of the extended axle. The pulleys 614A, 614B, 616A, 616B are arranged so as to form a first set of pulleys 614B, 616B and a second set of pulleys 614A, 616A. The first set of pulleys 614B, 616B are on one side of the second yoke 610, and the second set of pulleys 614A, 616A are on the other side of the second yoke 610. As shown in FIG. 11, the pulleys 614A, 614B are outer pulleys and the pulleys 616A, 616B are inner pulleys, with reference to the orientation of the pulleys as shown in FIG. 11. It should be appreciated that a set of pulleys can include any suitable number of pulleys, including one, two, or more than two (e.g., three, four, five, six, etc.) pulleys.

As further shown in FIG. 11, the brackets 610A, 610B of the second yoke 610 are coupled to a third set of pulleys 618A, 618B that are arranged along an axis 620 extending through the brackets 610A, 610B. The tool 600 can be actuated to move one or both of the jaws 606A, 606B in a variety of ways around the axis 620. For example, the jaws 606A, 606B may open and close relative to each other. The jaws 606A, 606B can also rotate together as a pair to provide a yaw motion and/or a pitch motion of the tool 600. The surgical system can include various cables appropriately configured to enable motion of the jaws 606A, 606B.

Figure 12A:
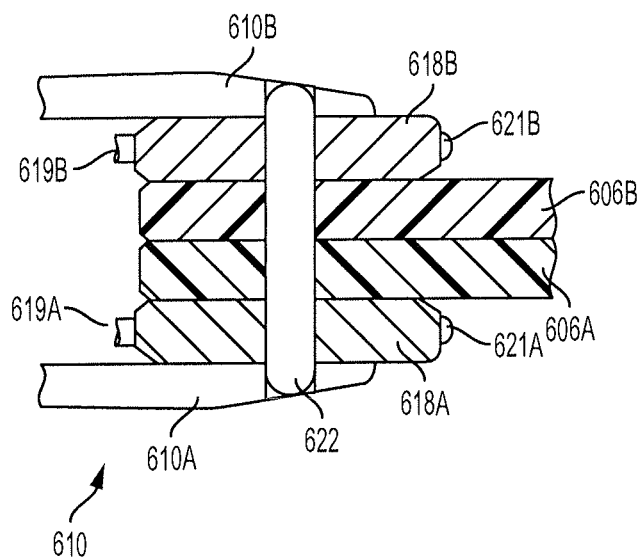
FIG. 12A is a cross-sectional view of a portion of the electromechanical tool of FIG. 11 which can have a force limiter associated therewith.

As shown in FIG. 11 and further shown in FIG. 12A, illustrating a portion of the tool 600 in cross-section along the axis 620, each of the pulleys 618A, 618B can be configured as a disk or gear having a bore or a groove that has a respective cable of the cables 619A, 619B extending therethrough. In the example illustrated, the cables 619A, 619B extend through the pulleys 618A, 618B such that the cables 619A, 619B are prevented from slipping or sliding relative to the pulleys 618A, 618B via beads 621A, 621B (or other components) coupled to or integrally formed with the ends of the cables 619A, 619B. A person skilled in the art will appreciate that the cables 619A, 619B can be coupled to the pulleys 618A, 618B in a number of different ways.

Figure 12B:
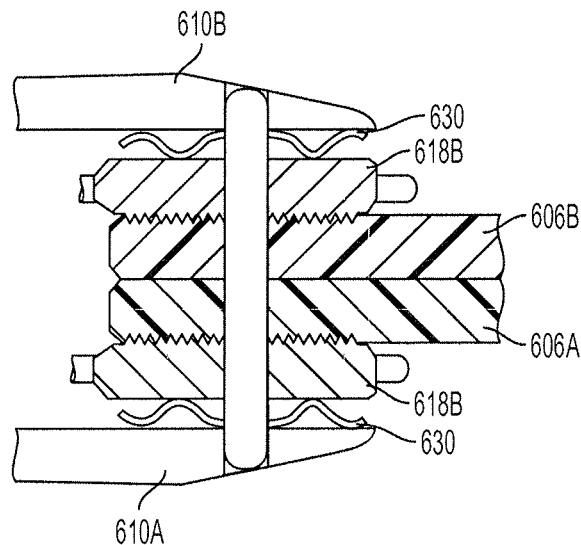
FIG. 12B is a cross-sectional view of a portion of the electromechanical tool of FIG. 11 which can have a force limiter associated therewith, additionally showing a spring.

As shown in FIG. 12A, the second yoke 610 can include an extended axle or pin 622 that extends along the axis 620. The pin 622 can be removably coupled with the second yoke 610 or it can be monolithically and/or integrally formed therewith. As shown in FIGS. 11, 12A, and 12B, the jaws 606A, 606B of the tool 600 can be coupled to the second yoke 610 via the third set of pulleys 618A, 618B, such that the jaws 606A, 606B can rotate about the axis 620. The pin 622 extends along the axis 620 and can allow rotation of the jaws 606A, 606B and the pulleys 618A, 618B along the axis 620 that coincides with the axis of the pin 622. The pin 622 can be coupled to the brackets 610A, 610B in a number of ways (e.g., laser welded into the brackets, swaged, riveted, screwed into place, etc.).

FIG. 12A illustrates a portion of the tool 600 that can have a force limiter associated therewith. The force limiter in the form of a slip clutch can be formed by the virtue of the configuration of the components of the tool 600 shown in FIG. 12A. Thus, in use, as the jaws 606A, 606B close to engage tissue therebetween, the pulleys 618A, 618B move the jaws 606A, 606B through friction, until a certain magnitude of friction is reached, beyond which the pulleys 618A, 618B slip with respect to the jaws 606A, 606B, respectively, thereby creating a slip clutch force limiter. In this example, the threshold (e.g., maximum allowed) level of friction corresponds to a maximum compressive force applied by the jaws. In other words, when a predetermined value of friction is achieved, continued rotation of the pulleys 618A, 618B fails to advance the jaws 606A, 606B further towards each other.

FIG. 12B additionally illustrates that the portion of the tool 600 shown in FIG. 12A can include springs 630 (e.g., wave springs or other resilient component(s)) disposed between a bracket of the brackets 610A, 610B and at least one of the drive pulleys 618A, 618B. Although two springs 630 are shown in FIG. 12B, it should be appreciated that only one of the springs can be present. The spring(s) 630 can be configured to force the pulleys 618A, 618B against the jaws 606A, 606B so that the respective teeth of the jaws and the pulleys are operatively engaged. As the jaws 606A, 606B close, the pulleys 618A, 618B move the jaws 606A, 606B through friction, until a certain level of friction is reached, beyond which the spring force is overcome and the pulleys 618A, 618B slip with respect to the jaws 606A, 606B, respectively.

Figure 13A:
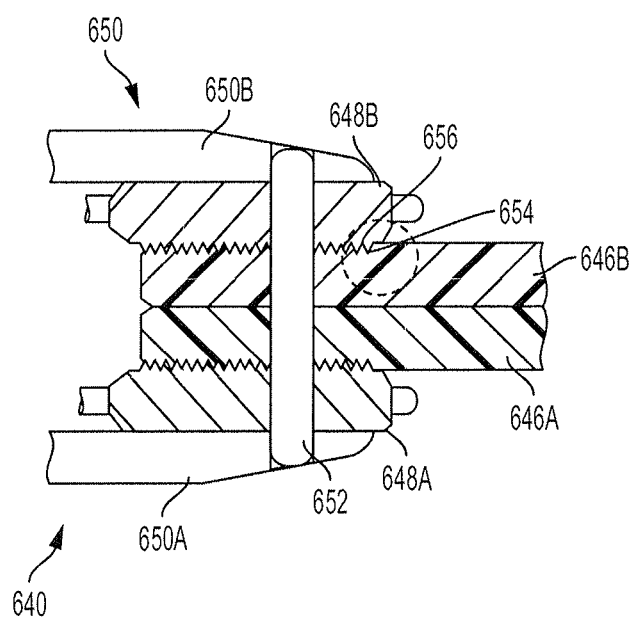
FIG. 13A is a cross-sectional view of one embodiment of a portion of an electromechanical tool having a force limiter associated therewith.
Figure 13B:
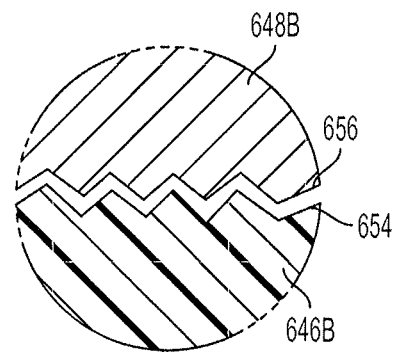
FIG. 13B is an enlarged cross-sectional view of the portion of the electromechanical tool of FIG. 13A, illustrating the force limiter.
Figure 14:
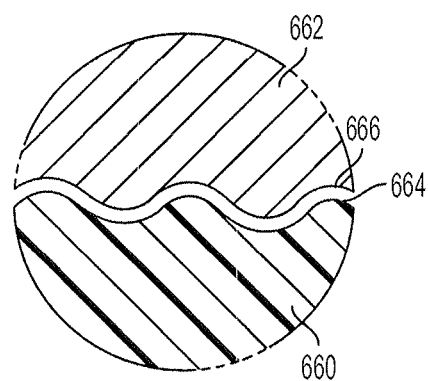
FIG. 14 is an enlarged cross-sectional view of another embodiment of a portion of an electromechanical tool having a force limiter associated therewith.

FIGS. 13A, 13B, and 14 illustrate other examples of force limiters associated with an electromechanical tool. In these examples, a jaw and a pulley's disk or gear are engageable via a ratchet-tooth-type mechanism such that the jaw and the gear move together until a certain threshold amount of force is reached, at which point they "slip" with respect to each other and become disengaged from each other.

FIGS. 13A and 13B illustrate a portion of an electromechanical tool 640 that is similar to electromechanical tool 600 in FIGS. 11 and 12A. Thus, like tool 600, the tool 640 includes jaws 646A, 646B, drive pulleys 648A, 648B, and brackets 650A, 650B of a yoke 650, all of which are movably held together via a pin 652. As shown in FIG. 13A, and in more detail in FIG. 13B illustrating a portion of FIG. 13A, the jaws 646A, 646B have teeth 654 on a side thereof facing the pulleys 648A, 648B, and the teeth 654 can be configured to engage with corresponding teeth 656 formed on a side of the pulleys 648A, 648B facing the 646A, 646B. The teeth 654, 656 form a ratchet mechanism similar to the slip clutch in FIG. 12B. The ratchet mechanism can control a slippage of the jaws 646A, 646B with respect to one another. Because of the way the teeth 654, 656 are configured to engage with each other, such ratchet mechanism can be advantageous in surgical environments where fluids (e.g., blood and other fluids) can affect a friction between the jaws 646A, 646B and between the jaws 646A, 646B and the pulleys 648A, 648B in various ways. Specifically, the configuration of the teeth 654, 656 can enable limiting the force applied by the jaws 646A, 646B in a more controlled and accurate manner.

The jaws and pulleys of an electromechanical tool can frictionally engage so as to form a force limiter having a number of different configurations. In the example of FIGS. 13A and 13B, the teeth 654, 656 are configured as sharp-angled teeth. FIG. 14 illustrates another example of a tool where a force limiter is associated with the jaws and where teeth have a more curved configuration. Specifically, as shown in FIG. 14, illustrating a portion of the tool, a jaw 660 and a pulley 662 are engageable via respective teeth 664, 666 that have a wavy curved surface. Other jaw and pulley of the electromechanical tool can be configured to engage in the same or similar manner.

As mentioned above, teeth formed on surfaces of the jaws and pulleys facing each other can have various configurations, including sharp, curved, angled in any manner, and any other types of teeth forming regular or irregular patterns. Furthermore, the surface features formed on surfaces of the jaws and pulleys facing each other can be other than teeth. As a further variation, the surface features can be formed on opposing slip plates or other components disposed between a jaw and pulley, rather than on the surfaces of the jaw and the pulley. Furthermore, although not shown in FIGS. 13A, 13B, and 14, the tools shown in these figures, as well as any other tools having a force limiter, can have a spring (e.g., wave spring or other spring such as, e.g., springs 630 shown in FIG. 12B) or other mechanism(s) configured to compress the components of the tool together.

Figure 15:
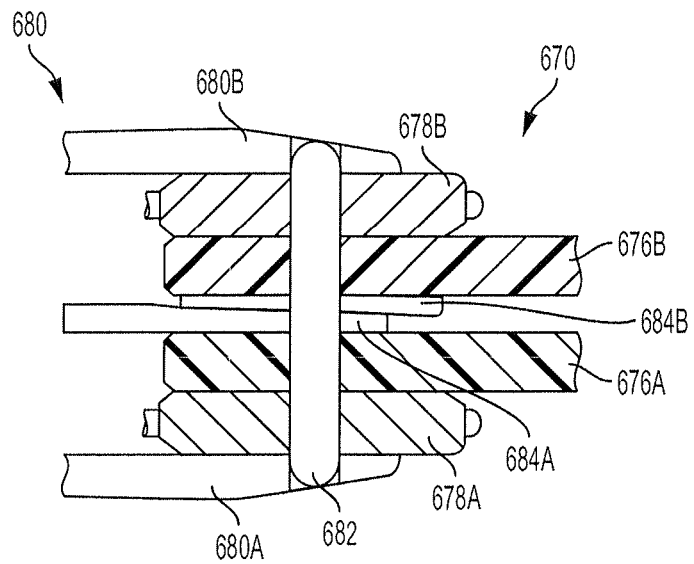
FIG. 15 is a perspective cross-sectional view of one embodiment of a portion of an electromechanical tool having a force limiter in the form of spacer shims associated therewith.

FIG. 15 illustrates a further example of a force limiter including one or more spacer shims or slip plates 684A, 684B disposed between jaws of an end effector of an electromechanical tool. An electromechanical tool 670 of the type shown in FIG. 15 can be similar to electromechanical tool 600 in FIGS. 11 and 12A. Thus, like tool 600, the tool 670 includes jaws 676A, 676B, drive pulleys 678A, 678B, brackets 680A, 680B of a yoke 680, and a pin 682.

As shown in FIG. 15, the tool 670 can have the spacer shims in the form of slip plates 684A, 684B disposed between the jaws 676A, 676B in a way such that they do not interfere with operation of the jaws 676A, 676B. Although not shown in FIG. 15, the jaws 676A, 676B can be angled toward one another. The slip plates 684A, 684B can be configured to have opposed complementary ramped surfaces. The relative position of the slip plates 684A, 684B is adjustable so as to increase or decrease the threshold force. In the example shown in FIG. 15, movement of the slip plates towards one another increases the threshold force, while movement of the slip plates away from one another decreases the threshold force. The slip plates 684A, 684B can be moved and adjusted via a motor, a solenoid, a mechanical controller, a robotic controller, manually, or in any other manner or via a combination of different ways. For example, in at least some embodiments, the slip plates 684A, 684B can be adjusted manually or automatically via a screw or other mechanism (not shown).

The slip plates 684A, 684B can have various configurations. In the example of FIG. 15, the slip plates 684A, 684B are configured as inclined plates, with the plate 684A being inclined toward the distal-most end of the jaws and the plate 684B being inclined in the opposite direction. It should be appreciated that the inner surfaces of the jaws 676A, 676B can be angled toward each other or configured in other manner such that the slip plates 684A, 684B do not interfere with operation of the jaws 676A, 676B as they move to engage tissue and/or for other purposes. As discussed above, a spring or other component can optionally be positioned between the bracket and pulley.

Figure 16:
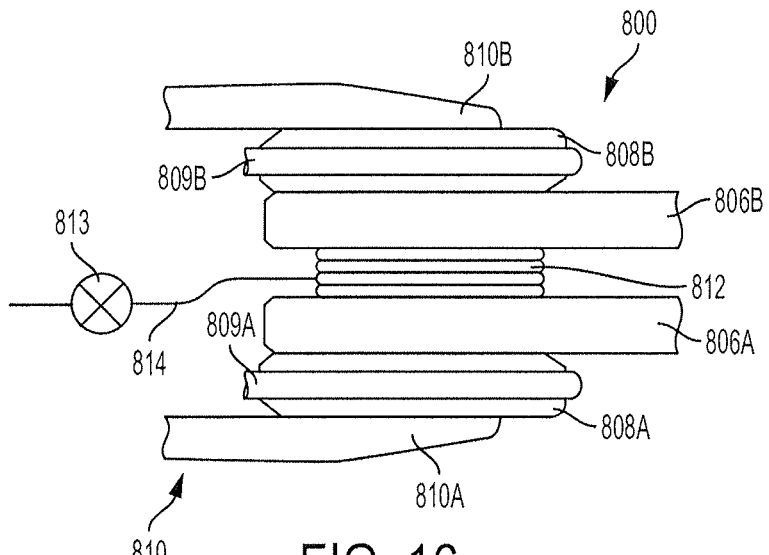
FIG. 16 is a perspective cross-sectional view of one embodiment of a portion of an electromechanical tool having a force limiter in the form of bellows associated therewith.

FIG. 16 illustrates an example of an electromechanical tool 800 that has a force limiter in the form of a bellows 812 disposed between jaws of the tool's end effector. The electromechanical tool 800, which can be similar to electromechanical tool 600 (FIGS. 11 and 12A), includes jaws 806A, 806B, drive pulleys 808A, 808B, brackets 810A, 810B of a yoke 810, and a pin (not shown). FIG. 16 also illustrates cables 809A, 809B extending through the drive pulleys 808A, 808B. The bellows 812 disposed between the jaws 806A, 806B is configured to controllably deform (e.g., expand or contract) so as to increase or decrease a friction force between the jaws 806A, 806B and the pulleys 808A, 808B. The bellows 812 can be operated, for example, by fluid the flow of which in or out of the bellows is controlled by a valve 813 and via a conduit 814. The bellows 812 thus expands or contracts to thereby increase or decrease the frictional force between the jaws and the pulleys. As discussed above, the tool 800 can optionally have a spring or other component disposed between the bracket and the pulley.

Figure 17:
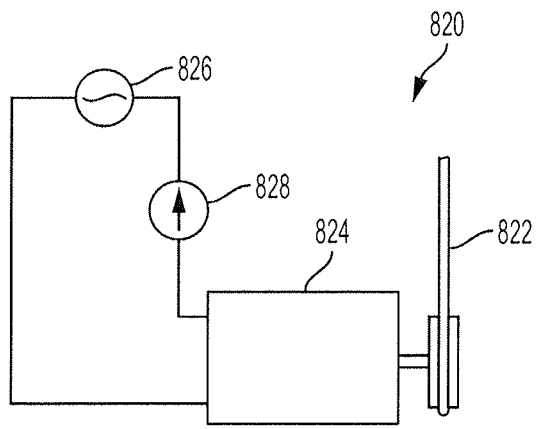
FIG. 17 is a schematic diagram illustrating a force limiter implemented in software.

The force limiter in accordance with the described techniques can be implemented in a number of ways. In some embodiments, for example, it can be implemented via software, e.g., the form of what is referred to as a software clutch. Such a software clutch can generally be formed by components that automatically control force applied by one or more cables driving an end effector of an electromechanical tool. An example of such an embodiment of a force limiter 820 is shown in FIG. 17 illustrating a cable 822 that can be operated by applying a desired amount of tension thereto to thereby operate an end effector of an electromechanical tool (not shown). A person skilled in the art will understand that two or more cables can be used to operate the end effector, and that only one cable 822 is shown in FIG. 17 by way of example only. The force limiter 820 can include a motor 824 that is driven by a drive voltage 826. The motor torque is proportional to current applied thereto and the force of the cable 822 is proportional to the motor torque. A current meter 828 can be used to control the current such that limiting the current causes a force applied by the cable 822 (via tensioning thereof) to be limited. In this way, the end effector driven via the cable 822 is controlled to apply a force to tissue that does not exceed a certain threshold value.

Software-based force-limiting control techniques can be applied to various components that are used to operate jaws or other end effectors of an electromechanical surgical tool. For example, the force limiter can be in the form of a pseudo-clutch having magnets. The magnets can be incorporated into suitable locations on opposed surfaces of the jaws (e.g., jaws 606A, 606B of tool 6000 in FIG. 11). The magnitude of the threshold force can be controlled by controlling the amount of current through the coil.

The examples described above in connection with FIGS. 11, 12A, 12B, 13A, 13B, and 14-17 illustrate a force limiter associated with an electromechanical surgical tool. In some embodiments, as mentioned above, force limiters of the type described above can be adapted to use with an electromechanical arm to limit the force that is applied as a result of moving the electromechanical arm. Thus, components of the arm that move with respect to each other when the arm is operated can be controlled to interact with a frictional force created therebetween that is limited to a certain threshold value.

Regardless of the particular implementation of a force limiter, it can be configured to control application of a force by an electromechanical arm or by an electromechanical surgical tool such that the force does not exceed a threshold force value.

The threshold force value can be established in a number of different ways. In some embodiments, the threshold force value can be established based on a user input which can be received in various ways. For example, the user input can be received with respect to one or more mechanical components of a force limiter, by adjusting settings and/or position of the component(s). The force limiter can include or can be associated with a specific force limiter adjustment mechanism that can be configured to receive input with respect to setting and/or adjusting the threshold force value. For another example, the user input can be received via a user interface, such as a user interface of system 408 shown in FIG. 6. The user interface can be configured to receive a user input in a suitable format, and one or more parameters relating to the threshold force value can be generated and transmitted to the force limiter.

Regardless of the specific way in which it is implemented, the threshold force value can be preselected prior to operation of the surgical system. Furthermore, in some cases, the threshold force value can be adjusted as the surgical instrument is being operated, or at a time period when the instrument is not in use. The threshold force value can be selected from a certain number of discrete and/or continuous values. In some embodiments, the threshold force value can be set in response to receiving user input indicating a selection of a certain mode, such as a tissue type mode, a surgical experience mode, etc.

Figure 18:
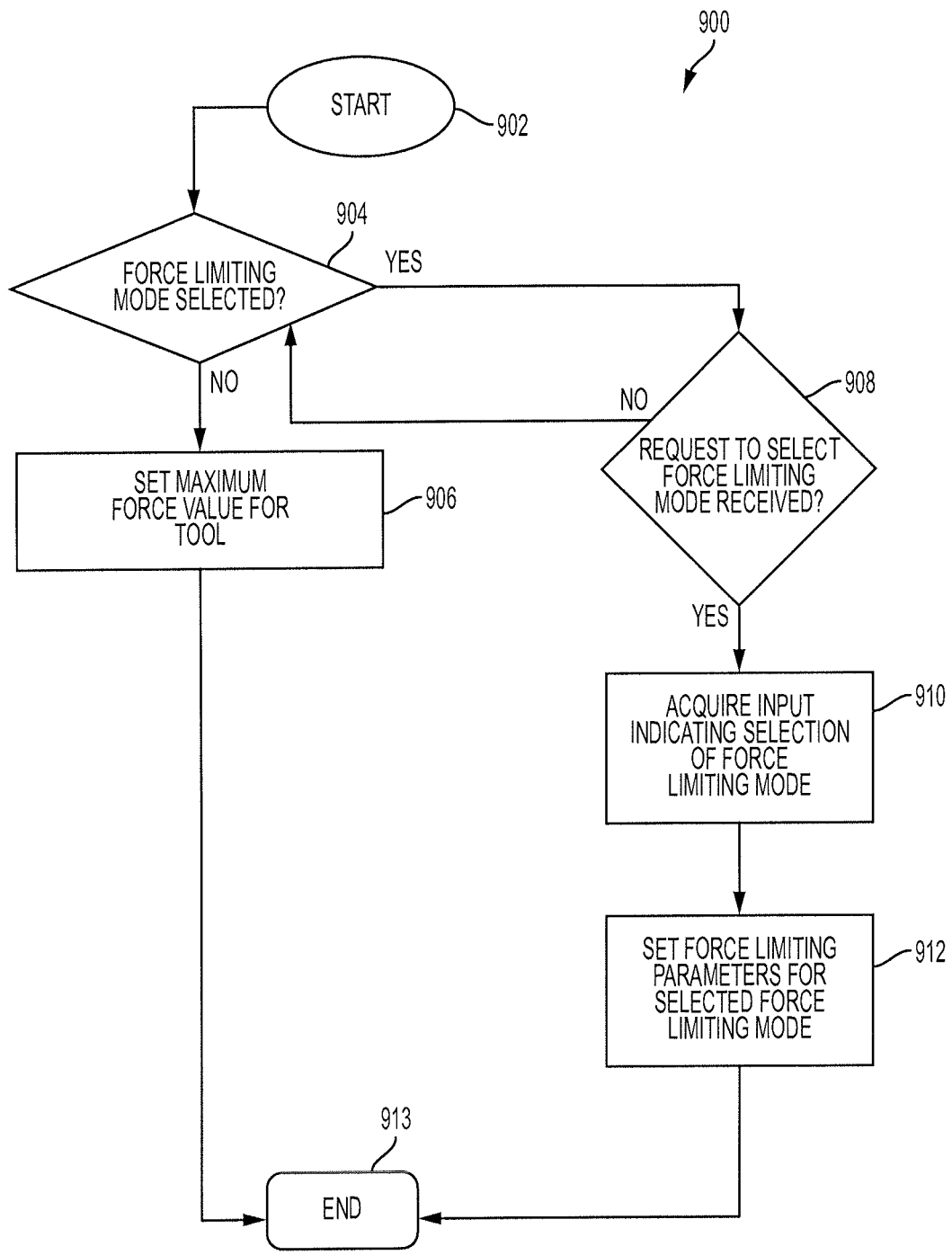
FIG. 18 is a flowchart illustrating an example of a process of selecting a threshold force value for a force limiter of a tool of a surgical instrument in accordance with some embodiments.

FIG. 18 is a flowchart illustrating an example of a process 900 of selecting a threshold force value for a force limiter of a tool of a surgical instrument in accordance with some embodiments. The process 900 can be implemented by a suitable controller, which can be, for example, a computing device that can be communicatively coupled to a display configured to render a user interface. The computing device can be configured to receive user input with respect to selection of threshold force values via the user interface. Furthermore, in some embodiments, a threshold force value can be selected via one or more control features (e.g., knobs, switches, and other features) associated with the force limiter. Such control features can be coupled to the force limiter directly or via other components, and they can be disposed at various locations with respect to the force limiter.

After the selection process starts at block 902 in a suitable manner (e.g., when an operation of the surgical instrument is initiated), it can be determined, at decision block 904, whether a force limiting mode is selected. This can be done in a number of ways. For example, the user interface can present a respective representation (e.g., graphical, textual, voice-based, etc.) and a suitable user input can be received with respect to this representation. When it is determined that the force limiting mode is not selected, the process 900 branches to block 906 where a maximum allowed force value for a tool can be set as the threshold force value.

As further shown in FIG. 18, when it is determined, at decision block 904, that the force limiting mode is selected, the process 900 can proceed to decision block 908 where it is determined whether a request to set up a certain force limiting mode is received. When the force limiting mode is not selected (e.g., no input with respect to selection of a mode is received), the process 900 can return to block 904. However, when the force limiting mode is selected, next, at block 910, an input can be acquired indicating a selection of a force limiting mode. The force limiting mode can be selected from a number of different modes. For example, one or more modes can correspond to a threshold force value suitable for certain tissue type(s) to be manipulated by the tool, or to a strength of a suture to be used. Additionally or alternatively, one or more modes can correspond to a threshold force value suitable for a certain level of experience of a surgeon. As another example, a "free selection" mode can be used in which a user input can be received indicating a setting of a threshold force to any desirable and appropriate value. Also, a mode can be selected from a set of preselected settings for a maximum force value, such as, for example, "high," "medium," and "low." The set of preselected settings can include any suitable numbers of settings. Any other modes can be used additionally or alternatively. The modes can be presented to a user in a manner that allows establishing a force limiting threshold in a more intuitive manner, such that a selection of a particular numerical value is not required. A desired mode can instead be selected and a force value associated with the selected mode can be then used for a force limiter.

After the input with respect to a selected mode is received at block 910 and the force limiting mode is thereby selected, the process 900 proceeds to block 912 where force limiting parameters can be set based on the selected force limiting mode. In this way, the force limiter is limited to a maximum force value. The process 900 can then end at block 913. It should be appreciated, however, that, in some embodiments, a threshold force value can be adjusted during operation of a surgical instrument. Further, a person skilled in the art will understand that the process 900 is shown by way of example only, as a threshold force value can be selected and adjusted in various other ways.

As mentioned above, a force limiter in accordance with the described techniques can have a number of different variations. The maximum force that the force limiter allows a tool or an arm associated therewith to apply can be adjusted. Furthermore, in some embodiments, a surgical instrument having a force limiter can be preset to a maximum force value that is not changeable by a surgeon. In such embodiments, multiple surgical instruments can be used, each having a certain maximum force value preset for its force limiter.

In some embodiments, one or more sensors of suitable type(s) can be associated with a force limiter. For example, a pressure sensor can be incorporated into surfaces of surgical tool's jaw that interact with one another to implement the force limiter. The force sensor can be associated with jaws of a working end of a surgical instrument, for example, if the instrument is to be used in environments where liquids (e.g., blood or other fluids) can interfere with proper functioning of the force limiter. For example, one or more force sensors can be used to monitor a force applied by the tool, and to provide feedback about the measured force which can be different from a force perceived by the force limiter, due to the additional friction created by the fluids. In this way, precision of operation of the force limiter in bloody fields can be improved.

A robotic surgical system can include one or more electromechanical passive arms coupled to an operating table or other platform and an electromechanical active arm coupled to the passive arm(s). The passive arm is used for rough positioning of the active arm; and, once generally positioned, the active arm, which has a surgical tool coupled distally thereto, can be more finely positioned to perform a surgery using the surgical tool.

Positioning and repositioning of the passive arm can be challenging, particularly during a surgical procedure when it has other components mounted thereto, and when timely and precise adjustment of the surgical system can determine the outcome of the surgery. To properly support the active arm, the passive arm needs to act as a sufficiently rigid mounting structure such that unintended perturbations or positional drift and sag in the system do not impact the required performance of the active arm and the surgical system in general. The passive arm also needs to be able to withstand the weight of the entire arm prior to and during a surgical procedure, so as to allow a user to easily position the passive and active arms without feeling the burden of the arms' weight. In other words, the passive arm should not be overly limp or expressively rigid, which will make it difficult to set and adjust its position.

Accordingly, the described system provides a way to control and adjust a stiffness of the passive arm. Specifically, the surgical system can be configured such that the passive arm's stiffness can be changeable during different stages of a surgical procedure. The passive arm can have two or more segments coupled via joints, and a friction (e.g., resistance of the joint(s) to rotation) of one, some, or all of the joints can be automatically adjusted based upon the degree of cantilever or extension of the passive arm. In this way, when the passive arm is being positioned, a change in an angle at the arm's joint is detected, and the friction of the joint is adjusted based on that angle. The adjustable magnitude of the friction force can be set based on the type of the passive arm, its weight and weight of components mounted thereon, and any other factors.

A joint of the passive arm can be associated with one or more components allowing its friction and thus the stiffness of the arm to be controlled. For example, the joint can be associated with a clutch mechanism or other component such as a mechanical brake, a fluidic brake, software-based friction control component(s), or any other suitable components. The passive arm joints can include mechanical springs or other similar components to provide joint's rotational stiffness that varies in proportion to an angular position of the joint that depends of a degree of extension of the passive arm.

The stiffness of the passive arm's joint arm can be controlled in a number of different ways. For example, the joint's stiffness can be selectively controllable by a user by manipulating one or more components on the arm, via mechanical linkages and/or adjustments made based on user input. Additionally or alternatively, the stiffness of the passive arm's joint can be controlled using software-based control, e.g., using an electronic feedback to the robotic system controller.

The joint can include various components that can control its friction, which affects a force required to move the arm. The components associated with the joint can be, for example, a mechanical brake, a fluidic brake, a clutch mechanism, or any other components. The one or more components can be controlled such that the friction of the joint can be automatically or manually adjusted proportional to an angle at the joint. The adjustment can be performed separately for each joint of the arm, for more than one joint, or for all joints of the arms that allow motion in one or more degrees of freedom.

In some embodiments, the mechanical stiffness can be controlled and adjusted using a clutch mechanism similar to mechanisms described in connection with FIGS. 11, 12A, 12B, 13A, 13B, 14, 15, 16, and 17. For example, a clutch mechanism in the form of slip plates, or a mechanism having any other suitable configuration, can be used. In some embodiments, additionally or alternatively, motors (e.g., motors 208 in FIG. 3) associated with the joints and operating to cause movement of the arm can be used to establish a torque limit and thus control a stiffness of the joints, as it is perceived by the user. A torque applied by the motor is controlled through the control of current supplied to the motor. Further, in some embodiments, a gear train system or other similar system can be used to control the torque applied by the motor.

In some embodiments, one or more of joints of an electrochemical arm (e.g., joints 308 of arm 300 shown in FIGS. 4 and 5 above) also include a force sensor (not shown in FIGS. 4 and 5). When there is an attempt to move the arm at a joint, for example, when a user begins moving the arm and thus applies a force to the arm in a certain direction, this attempt is detected by the force sensor disposed at that joint. In response, a motor driving the arm is caused to move the arm in the direction of the force applied by the user until the force is no longer applied to the arm (e.g., when the user stops moving the arm). One or more of any suitable force sensors can be disposed at a joint. In some embodiments, data from sensors disposed at each joint of an arm is acquired, and a three-dimensional force applied to all of the joints of the arm is determined based on this sensed data. In this way, motors configured to drive the entire arm can be controlled to move the arm in a concerted manner, such that an appropriate amount of force is applied to the arm to move it in a desired manner.

Figure 19:
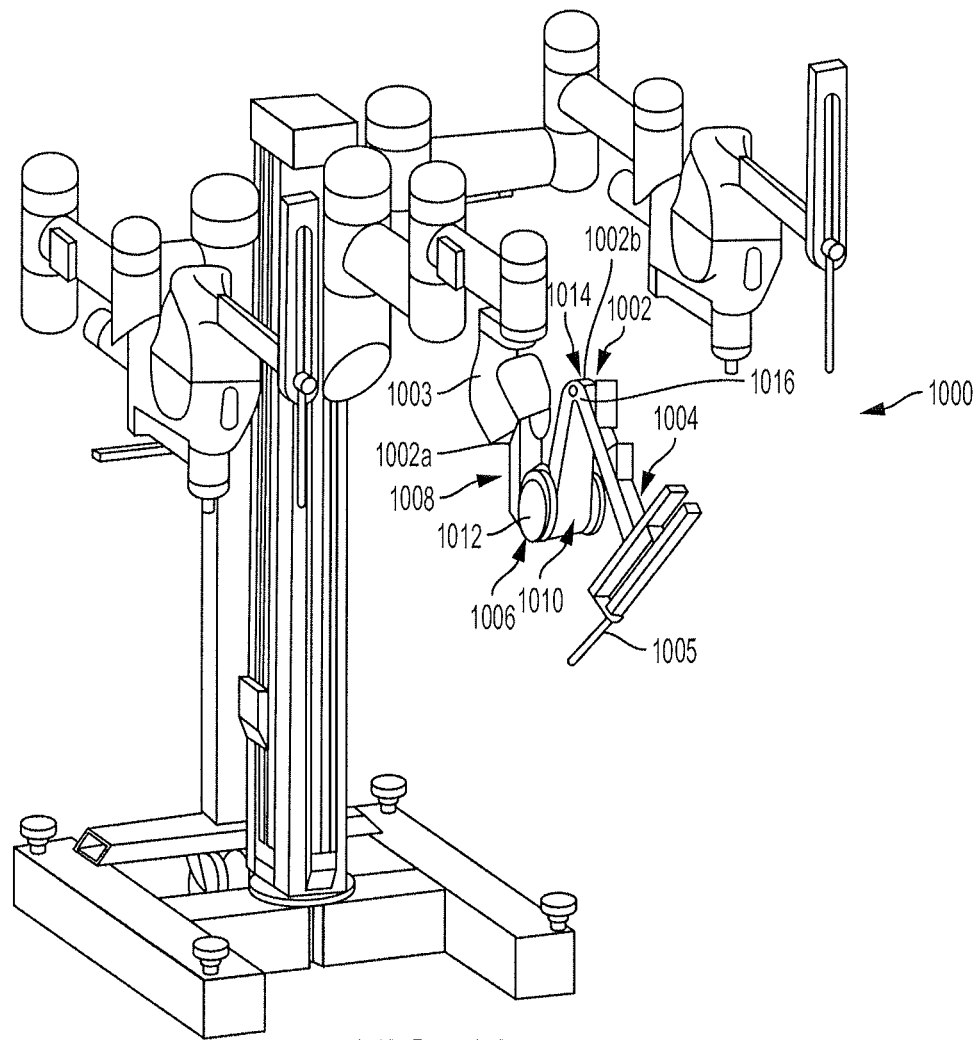
FIG. 19 is a perspective view of a robotic surgical system in which a stiffness of an electromechanical passive arm is controlled in accordance with some embodiments.

FIG. 19 illustrates an example of a robotic surgical system 1000 including an electromechanical passive arm 1002 having a first end 1002a coupled to a fixture 1003 of the surgical system 1000, and a second end 1002b coupled to an electromechanical arm 1004 which can be an active arm. The passive and active arms 1002, 1004 can be modular such that they are reversibly coupled to one another and can be separated by a user, or they can be permanently attached to one another. In addition, it should be appreciated that one passive arm and one active arm are shown by way of example only, as the surgical system can include more than one passive arm and/or more than one active arm.

The passive arm 1002, which can have multiple degrees of freedom, can be used for gross or rough positioning of the active arm 1004. After it is positioned as desired, the passive arm 1002 can be locked at that position, which can be done manually (e.g., by manipulating a locking mechanism of the arm) or automatically, as described in more detail below. During a surgical procedure, the passive arm 1002 can be repositioned. The active arm 1004 includes motors such that it can be dynamically moved to perform a surgery.

The fixture 1003 can be any suitable support member or other component, suitable examples of which are well known to those skilled in the art.

The arm 1004 can have a surgical instrument 1005 mounted on a distal end thereof. As shown in FIG. 19, the electromechanical arm 1002 can have a joint 1006 between the first and second ends 1002a, 1002b. The joint 1006 connects first and second passive arm segments 1008, 1010. In this example, the second passive arm segment 1010 can move with respect to the fixture at the joint 1006. Thus, the second end 1002b of the passive arm 1002 is configured to move toward and away from the fixture 1003 such that an angle between the first and second arm segments 1008, 1010 increases as a distance between the second end 1002b and the fixture 1003 increases. The first passive arm segment 1010 can be fixed at a certain angle with respect to the fixture 1003 and the joint 1006.

As shown in FIG. 19, the joint 1006 between the first and second passive arm segments 1008, 1010 is in the form of a rounded joint. However, it should be appreciated that the joint 1006 can have various configurations. The joint 1006 can have a sensor 1012 associated therewith that is not shown separately in FIG. 19. The sensor 1012 can be an angle measurement sensor configured to sense an angle between the first and second passive arm segments 1008, 1010. The sensor 1012 can have any suitable configuration, and it can be in the form of any suitable angle measurement sensor, such as, for example, an optical encoder, magnetic encoder, a strain gage to measure the flexure of a suitable component (e.g., a metal strip) positioned so that it flexes depending on a measured value of an angle, or any other angle measurement sensor.

Figure 20:
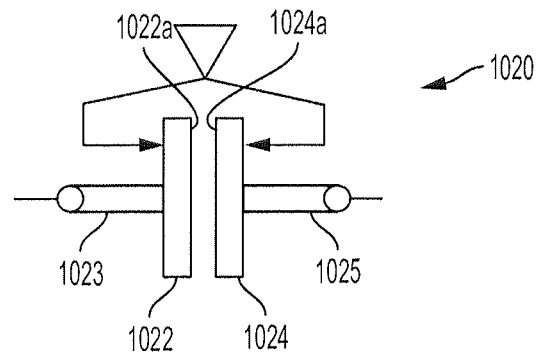
FIG. 20 is a schematic diagram of a clutch.

The joint 1006 associated with the sensor 1012 can house any number of clutch systems having any suitable configuration. A controller of the robotic surgical system can control the use of data acquired by one or more sensors, such as the sensor 1012, by the clutch system(s) of the surgical system. A conceptual example of a clutch is shown in FIG. 20. Regardless of their specific type, the one or more clutches are used to impart an appropriate amount of resistance to motion of the arm 1002 at the joint 1006. Thus, the clutch is controlled such that, depending on the angle between the first and second passive arm segments 1008, 1010 (e.g., as measured by the sensor 1012), a corresponding amount of clutch resistance affects the motion of the arm 1002. In this way, when the second passive arm segment 1010 is moved, the segment 1010 can be facilitated to move in a desired manner while unintentional movements of the arm and its associated components due to its weight are prevented.

The surgical system 1000 can include any other suitable sensors used to detect that the passive arm 1002 is being moved and/or to measure an angle between the first and second segments of the passive arm 1002. In the example illustrated, the surgical system 1000 further includes a gravity sensor 1014, as schematically shown in FIG. 19. The gravity sensor 1014 can be disposed at a joint 1016 connecting the passive arm 1002 and the active arm 1004, or in other locations on the passive arm 100. The gravity sensor 1014 can sense an angle at the joint 1016 between the first and second segments of the passive arm 1002 by determining a direction of a gravitational force experienced by the second passive arm segment 1010 relative to the first passive arm segment 1008.

Furthermore, additionally or alternatively, the surgical system 1000 can include more than one gravity sensor for determining angles between arms and their segments and/or orientations of the arms and the segments. For example, in some implementations, a first gravity sensor can be disposed on the first passive arm segment 1008 and a second gravity sensor can be disposed on the second passive arm segment 1010. Data acquired by the first and second gravity sensors can be used to determine a direction of gravity relative to each of the passive arm segments 1008, 1010 and thus an angle between the passive arm segments 1008, 1010, as well as the orientation of each of the arm segments 1008, 1010 relative to gravity.

Although not shown in FIG. 19, it should be appreciated that sensor(s) similar to the sensors 1012, 1014, or sensor(s) of any other type, can be included in the system 1000 and used to determine an angle between the passive arm 1002 and the active arm 1004. Data acquired by such sensors can be used to determine a distance to which the active arm 1004 is extended (or cantilevered) which is, in turn, used to determine how much frictional resistance the clutches or other friction controlling mechanism(s) should supply.

In some embodiments, in addition to or instead of clutches, the surgical system can include motors that are controlled to prevent unintended motion of joints of an arm. In such embodiments, a torque of the motor can be determined, and the acquired information can be correlated to an expected torque that is anticipated based on an angle of the arm. Thus, when a user tries to reposition the arm by moving it at a joint, the increased force on that joint is sensed and recognized as a reposition command. The motor(s) can then cause the force that the user needs to apply to reposition the arm to be reduced. In this way, the motors facilitate the user's operation of the arm while helping to ensure that the arm can be moved in a desired manner, without excessive effort on the user's part.

As mentioned above, one or more clutches associated with joints of an arm can have a number of different configurations. FIG. 20 illustrates an example a friction clutch 1020 that can be associated with a joint. The clutch 1020 can include clutch disks 1022, 1024 coupled to respective shafts 1023, 1025. For example, referring back to FIG. 19, if the clutch is disposed at the joint 1006, the shaft 1023 can be coupled to the arm segment 1008 whereas the shaft 1025 can be coupled to the arm segment 1010. As shown in FIG. 20, a surface 1022a of the disk 1022 faces a surface 1024a of the disk 1024 such that when the surfaces 1022a, 1024a are in contact and move with respect to one another a friction is created therebetween. The clutch disks 1022, 1024 are brought closer together by applying force thereto when rotational friction and resistance to movement at the joint are increased, based on an angle at the joint.

Figure 21:
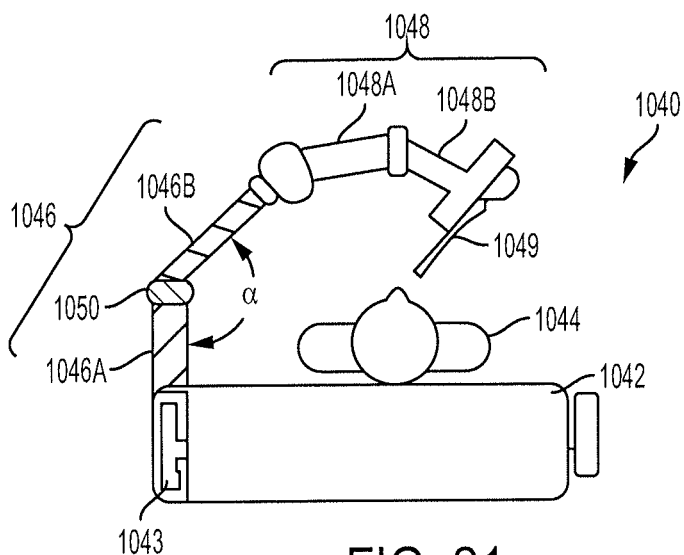
FIG. 21 is a perspective view of a robotic surgical system in which a stiffness of a passive arm is controlled in accordance with some embodiments.

In the described techniques, the friction of the joint is adjusted based on an angle at the joint. FIG. 21 illustrates a robotic surgical system 1040 including an operating room table 1042 that can have a patient 1044 positioned thereon, a passive electromechanical arm 1046 and an active electromechanical arm 1048. The active arm 1048 has a surgical tool 1049 coupled thereto that is configured to perform an operating procedure on the patient 1044.

The passive arm 1046 has first and second passive arm segments 1046A, 1046B that are movably coupled to one another by a mechanical joint 1050. The first and second passive arm segments 1046A, 1046B are disposed at an angular orientation with respect to one another, thus forming an angle alpha (α), as shown in FIG. 21.

When the surgical system 1040 is not in use, the passive arm 1046 can be stowed at the operating table 1042, e.g., alongside bed rails 1043 of the operating table 1042. At that time, the first and second passive arm segments 1046A, 1046B are folded against one another, and the angle α is therefore small (e.g., less than 5 degrees). To prepare the surgical system 1040 for the surgery, the passive arm 1046 is unfolded and is positioned such that it hovers over the patient 1044 in a bridge-like manner. As a result, the second passive arm segment 1046B is moved away from the first passive arm segment 1046A (and therefore away from the rail 1043 or other fixture to which the arm segment 1046A is coupled), and the angle α increases. The load (rotational moment) that the passive arm 1046 exerts on the joint is proportional to the angle α. Thus, a stiffness of the joint 1050, which depends on friction created therein, corresponds to the angle α. The passive arm 1046 is therefore configured to be gravity-balanced and self-supporting. In other words, the passive arm has appropriate and adjustable amount of resistance built therein such that it can be moved in a desired manner, independent of a load applied thereto (e.g., by the active arm and/or other components attached thereto). Thus, the passive arm 1046 is configured to have a sufficient stiffness of the joint 1050, such that the passive arm 1046 can be easily adjusted under the load caused by its own weight and the weight of the active arm 1048 and/or other components coupled thereto.

As indicated above, the angle α determines the stiffness of a joint of a passive arm (e.g., the joint 1050 in FIG. 21) as determined by a friction at the joint. The joint stiffness is adjustable depending on an angle at the joint to counteract gravity-induced loads on the arm at that angle. As shown in FIG. 21, the passive arm 1046 has load applied thereto by the active arm 1048 and the surgical tool 1049. The angle α can be proportional to the joint's stiffness, or it can vary in other ways depending on the joint's stiffness. The dependency of the joint's stiffness on the angle α can be linear or non-linear. When the angle α increases from 0° to 90°, the passive arm is positioned more horizontally (and the passive arm is therefore closer to the fixture at the operating table to which it is coupled). As the angle α increases up to about 90°, the joint's stiffness also increases. Once the angle α reaches 90° and may increase further, the passive arm is positioned more upright and thus requires less resistance at its joint. Thus, as the angle α becomes larger than 90°, the joint's stiffness decreases.

Referring back to FIG. 21, different magnitudes of friction of the joint 1050 can be required depending on a deployment configuration (e.g., an angle at the joint 1050) of the passive arm 1046 and at different phases of the robotic surgery. Accordingly, the passive arm 1046 can be configured such that a friction of the joint 1050 is adjustable and a stiffness of the passive arm 1046 is controllable by a user (e.g., a surgeon) operating the passive arm 1046. Additionally or alternatively, the friction of the joint 1050 can be controlled via a software-based control, e.g., via feedback signals provided to a robotic controller (e.g., controller 206 in FIG. 3 or any other controller). As another option, the friction of the joint 1050 can be controlled automatically by utilizing one or more components associated with the joint 1050, such as, for example, a clutch mechanism as described above, or any other mechanism (e.g., a mechanical brake, a fluidic brake, etc.).

In use, unless it is being adjusted, the passive arm is typically locked at a desired position. The passive arm can be locked manually, by using a locking mechanism associated with the arm. Additionally or alternatively, in some implementations, the passive arm is "locked" when its stiffness is sufficiency high to preclude its movement without a further force applied thereto. For example, after a user (e.g., a surgeon) moves the passive arm to position it, the system determines that the arm is no longer being moved, and its stiffness can be increased accordingly. This can also occur when the passive arm is locked via a suitable locking mechanism—e.g., when the arm is locked, the stiffness of component(s) controlling a friction of the arm's joint can be set to a "locked" value. Accordingly, the stiffness of the "locked" passive arm is greater than the stiffness that is desirable during arm positioning.

Thus, regardless of the specific way in which the passive arm is "locked," its stiffness is in an increased condition when it is stationary. In this way, a desired position of the passive arm, and therefore position of components mounted thereon, can be properly maintained. However, when the passive arm needs to be positioned again, its stiffness will decrease, to allow the positioning of the arm to be completed in a desired manner. The passive arm therefore can operate in different "modes"—a static ("locked") mode and a dynamic (positioning) mode.

Figure 22:
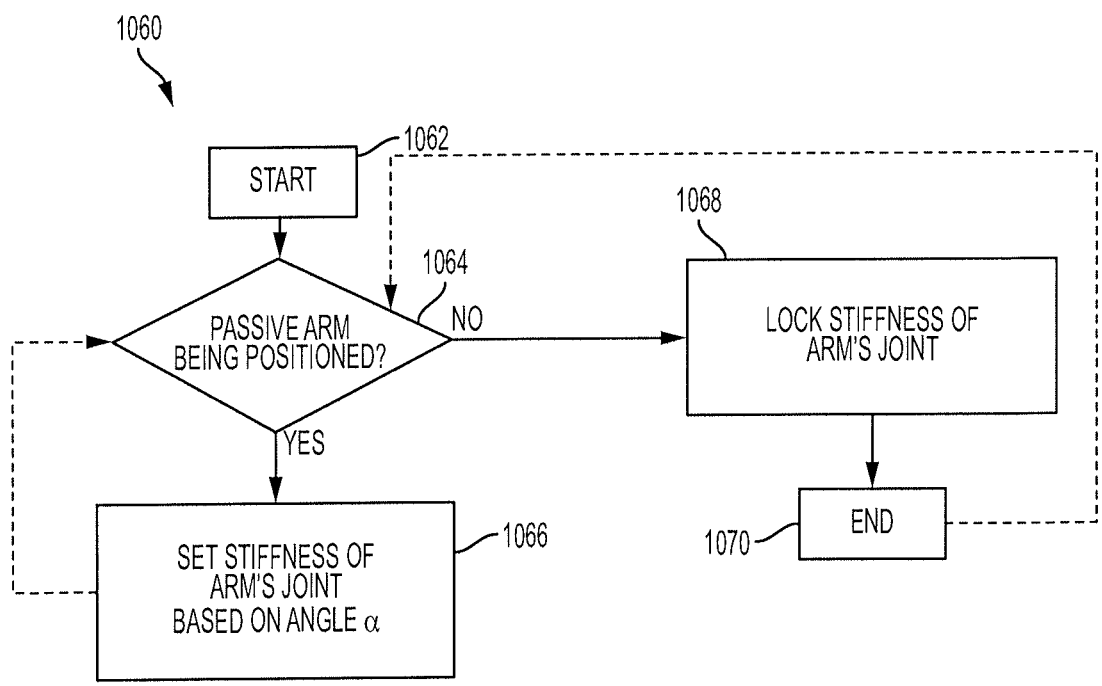
FIG. 22 is a flowchart illustrating an example of a process of setting or adjusting a stiffness of a passive arm.

FIG. 22 illustrates a process 1060 of setting or adjusting a stiffness of a passive arm (e.g., passive arm 1046 in FIG. 21, or any other arm) depending on whether the arm is being positioned. The process 1060 can be performed by a suitable controller (e.g., controller 206 in FIG. 3), or by any other component(s). For example, the process 1060 can be performed by one or more processors of a computing system (e.g., processor 102 of computer system 100 in FIG. 2). Furthermore, the process 1060 can be performed by one or more mechanical components, and/or by a combination of components of various types.

As shown, the process 1060 can start at block 1062 at any suitable time, for example as the passive arm is being moved. If it is determined, at decision block 1064, that the arm is being positioned, the process 1060 goes to block 1066 where a stiffness of the arm is set based on the arm's joint angle, referred to as "the angle α." Next, the process 1060 can return to block 1064 to monitor whether the arm is continued to be positioned or whether a desired position is established and the arm therefore need to be "locked" at that position.

As further shown in FIG. 22, if it is determined, at decision block 1064, that the arm is not being positioned, the process 1060 proceeds to block 1068 where a stiffness of the arm is set (increased) such that the arm is "locked" and prevented from inadvertent movement. At the locked position, the arm can have a stiffness that is greater than the gravitational force and active loads applied thereto. As shown in FIG. 22, the process 1060 can then end, at block 1070. However, it should be appreciated that the process 1060 can be performed continuously, such that, from block 1070, it can return to block 1064 to continue monitoring whether the arm is being positioned, as schematically shown in FIG. 22.

Figure 23:
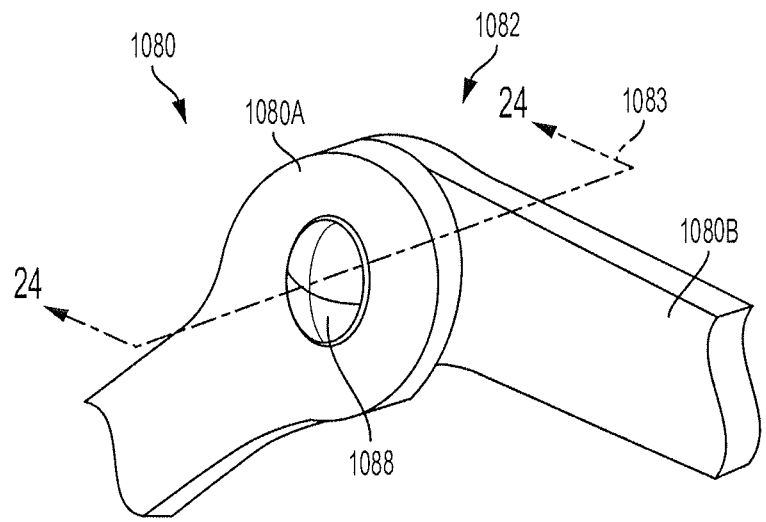
FIG. 23 is a perspective view of one embodiment of a portion of an electromechanical arm of a surgical system which has a force limiter associated therewith.
Figure 24:
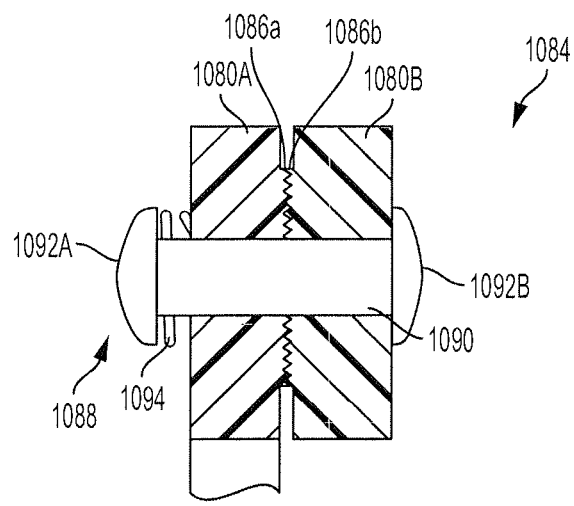
FIG. 24 is a perspective view of the force limiter associated with the electromechanical arm of FIG. 23.

As mentioned above, various mechanisms can be used to a control the friction of a passive arm's joint, and the mechanisms are not limed to clutches. FIGS. 23 and 24 illustrate an additional example of a mechanism that can be used to control and adjust a stiffness of an electromechanical arm 1080, such as a passive arm. The arm 1080 can include first and second segments 1080A, 1080B configured to move with respect to one another at a joint 1082 connecting them, along an axis 1083 extending through the joint 1082 as shown in FIG. 23. A mechanism 1084 is disposed between the first and second arm segments 1080A, 1080B.

In this example, the mechanism 1084, shown in FIG. 24 at a cross-section along the axis 1083, is in the form of a spring-loaded, friction-based mechanism. As shown in FIG. 24, surfaces of the portions of the segments 1080A, 1080B facing each other at the joint 1082 (as also shown in FIG. 23) include surface features 1086a, 1086b, such as ratchet teeth, configured to engage with each other. However, the ratchet teeth are shown by way of example only, as the surface features can be similar to features of force-limiting mechanisms descried above and shown in FIGS. 11, 12A, 12B, 13A, 13B, 14, 15, 16, and 17, or they can be any other surface features configured to releasably engage with each other.

A screw 1088 having a shaft 1090 and heads 1092A, 1092B can be used to hold the first and second arm segments 1080A, 1080B such that the shaft 1090 extends through connecting bores formed through the segments 1080A, 1080B, and the heads 1092A, 1092B prevent the shaft 1090 from coming out of the bores. One or both of the heads 1092A, 1092B can be removably coupled to the shaft 1090. As shown in FIG. 24, the mechanism 1084 can include a spring 1094, a portion of which is shown. The spring 1094 is configured to apply force to bring the segments 1080A, 1080B together at the joint 1082. One or both of the heads 1092A, 1092B can be configured to couple with an adjustment tool (e.g., a wrench or other tool) configured to tighten the spring 1094 to a desired degree of compression. The tighter the spring 1094 is clamped down, the higher the stiffness of the arm with respect to motion.

It should be appreciated that the spring can be adjusted in a variety of other ways. For example, in other implementations, the spring can be tightened via a solenoid or any other component(s) that can apply a force to the spring. In such implementations, the amount of stiffness associated with the arm's segments can be automatically adjusted by the robotic surgical system controlling the resistance to arm motion. The adjustment can also be done based on user input. As an example, a solenoid-based control mechanism can be configured to be manually adjusted, for example, via an electrical dial, slider, or any other feature(s) that a user (e.g., the surgeon or surgical staff) can adjust based on user's preferences.

In some embodiments, in addition to components described above, various other components can be used to control stiffness of a passive arm. For example, adjustable viscosity fluidic brakes (e.g., brakes based on magneto-rheological fluids) can be used. The arm stiffness can be adjusted by mechanically repositioning a magnetic field. For example, the friction of a joint of a passive arm can be adjustable using a fluidic break configured to position a magnetic field around the joint.

Furthermore, although the techniques for controlling an electromechanical arm's stiffness are described in connection with a passive arm stiffness control, it should be appreciated that a stiffness in an electromechanical active arm can also be controlled as described above or using similar techniques and components.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices and components described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the described techniques based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical system, comprising:
   an electromechanical arm configured for movement in multiple axes;
   an electromechanical tool mounted on the electromechanical arm and comprising first and second jaws configured to clamp tissue therebetween; and
   a force limiter associated with at least one of the electromechanical arm and the electromechanical tool and comprising a friction-based slip clutch mechanism configured to limit a force applied by at least one of the electromechanical arm and the electromechanical tool such that, when the force exceeds a threshold force value, the slip clutch mechanism disallows the first and second jaws from further advancement towards one another.

2. The system of claim 1, wherein the threshold force value is selected based on a user input.

3. The system of claim 1, wherein the threshold force value is selected automatically.

4. The system of claim 1, wherein the threshold force value comprises a maximum force value.

5. The system of claim 4, wherein the maximum force value is adjustable via a user input system.

6. The system of claim 4, wherein the maximum force value is adjustable via the force limiter associated with the electromechanical tool.

7. The system of claim 1, wherein the force limiter further comprises a force limiter adjustment mechanism.

8. The system of claim 7, wherein the slip clutch is coupled to at least one of the first and second jaws of the electromechanical tool, and the force limiter adjustment mechanism comprises at least one shim or at least one bellows disposed between the first and second jaws.

9. The system of claim 1, wherein the force limiter comprises at least one motor, and wherein current controlling torque of the at least one motor is used to control and limit the force applied by the electromechanical arm.

10. A method of operating a surgical system, the method comprising:
- positioning an electromechanical arm of the surgical system in proximity to a patient's body; and
- manipulating an electromechanical tool mounted on the electromechanical arm to perform a surgical function, wherein a force applied by at least one of the electromechanical arm and the electromechanical tool to cause movement of the electromechanical tool is limited to a maximum force by a slip clutch force limiter coupled to at least one of first and second jaws of the electromechanical tool.

11. The method of claim 10, comprising receiving an input indicating a value of the maximum force.

12. The method of claim 11, wherein the input comprises a user input received via a user interface of a computing device.

13. A surgical system, comprising:
- a passive arm having a first end configured to be coupled to a fixture and a second end, the passive arm having a joint between the first and second ends connecting first and second passive arm segments, the second end being configured to move toward and away from the fixture such that an angle between the first and second arm segments increases as a distance between the second end and the fixture increases; and
- an active arm coupled to the second end of the passive arm and configured to have a surgical instrument mounted on a distal end thereof;
- wherein the joint between the first and second ends of the passive arm has a stiffness that is configured to proportionally decrease as the angle between the first and second arm segments of the passive arm increases.

14. The surgical system of claim 13, wherein the stiffness of the joint is automatically adjusted based on the angle.

15. The surgical system of claim 13, wherein the stiffness of the joint is selectively controllable based on user input.

16. The surgical system of claim 13, wherein the stiffness of the joint is automatically adjustable via a software-based controller.

17. The surgical system of claim 13, wherein the joint has an angle measurement sensor coupled thereto and configured to measure the angle.

18. The surgical system of claim 14, wherein the joint has a force sensor coupled thereto and configured to sense a force applied to the passive arm.

19. The surgical system of claim 13, wherein the joint includes a clutch mechanism.

20. The surgical system of claim 13, wherein the system is configured to:
- in response to detecting that a force is being applied to the joint to position the passive arm and thereby change the angle between the first and second arm segments, reduce a resistance of the joint to allow the passive arm to be repositioned to an other position; and
- after the passive arm is repositioned, and in response to detecting that the force is no longer being applied to the joint, increase the resistance of the joint to cause the joint to remain in the other position.

21. A method of operating a surgical system, the method comprising:
- positioning an electromechanical surgical arm comprising a passive arm and an active arm coupled to the passive arm, the active arm having a surgical instrument mounted on a distal end thereof, the passive arm having first and second arm segments and a joint connecting the first and second arm segments in proximity to a patient's body, wherein the first arm segment has a first end coupled to a fixture and a second end coupled to the active arm; and
- changing a position of the passive arm by moving the second arm segment such that an angle between the first and second arm segments increases as a distance between the second end and the fixture increases, and such that a stiffness of the joint proportionally decreases as the angle increases.

* * * * *